(12) United States Patent
Shavit

(10) Patent No.: US 10,070,803 B2
(45) Date of Patent: Sep. 11, 2018

(54) SPIROMETER APPARATUS AND METHODS USEFUL IN CONJUNCTION THEREWITH

(75) Inventor: Nir Shavit, Giva'ataim (IL)

(73) Assignee: LUNGTEK LTD., Kfar Saba (IL)

( * ) Notice: Subject to any disclaimer, the term of this patent is extended or adjusted under 35 U.S.C. 154(b) by 518 days.

(21) Appl. No.: 13/389,092

(22) PCT Filed: Aug. 12, 2010

(86) PCT No.: PCT/IL2010/000651
§ 371 (c)(1),
(2), (4) Date: Feb. 6, 2012

(87) PCT Pub. No.: WO2011/018788
PCT Pub. Date: Feb. 17, 2011

(65) Prior Publication Data
US 2012/0136271 A1 May 31, 2012

Related U.S. Application Data

(60) Provisional application No. 61/233,681, filed on Aug. 13, 2009.

(51) Int. Cl.
*A61B 5/08* (2006.01)
*A61B 5/087* (2006.01)

(52) U.S. Cl.
CPC .......... *A61B 5/087* (2013.01); *A61B 2505/09* (2013.01)

(58) Field of Classification Search
CPC .................................................... A61B 5/087
(Continued)

(56) References Cited

U.S. PATENT DOCUMENTS

| 4,403,514 A | 9/1983 | Osborn |
| 5,038,621 A | 8/1991 | Stupecky |

(Continued)

FOREIGN PATENT DOCUMENTS

| CN | 2367251 Y | 8/2000 |
| RU | 73600 U1 | 5/2008 |
| WO | 2007/127340 A2 | 11/2007 |

OTHER PUBLICATIONS

Evenly definition (http://www.thefreedictionary.com/evenly).*
http://en.wikipedia.org/wiki/Spirometry, Jul. 22, 2009.

*Primary Examiner* — Christian Jang
*Assistant Examiner* — Mitchell E Alter
(74) *Attorney, Agent, or Firm* — Avery N. Goldstein; Blue Filament Law PLLC

(57) ABSTRACT

Spirometer apparatus comprising main inhale-exhale tube having first end, main interior, and second open end, a plurality of smaller tubes intersecting said main-inhale exhale tube at first and second respective locations and having a plurality of smaller interiors respectively, the first location being closer to the first end than is the second location, wherein each of the smaller interiors are in fluid communication with the main interior solely via at least one aperture formed in each of the intersecting tubes at locations facing said second end, the intersecting tubes having first and second external cross-sections, the main tube having first and second internal cross-sections, wherein said first external cross-section is smaller than said first internal cross-section, said second external cross-section is smaller than said second internal cross-section, and wherein said second external cross-section is smaller than said first external cross-section, and a differential pressure sensor sensing the pressure drop.

17 Claims, 23 Drawing Sheets

(58) Field of Classification Search
USPC .......................................................... 600/538
See application file for complete search history.

(56) References Cited

U.S. PATENT DOCUMENTS

| | | | |
|---|---|---|---|
| 5,137,026 A * | 8/1992 | Waterson et al. .............. | 600/538 |
| 5,913,249 A * | 6/1999 | Weckstrom ............ | A61B 5/087 |
| | | | 73/861.52 |
| 6,004,277 A | 12/1999 | Maharaj et al. | |
| 6,058,787 A | 5/2000 | Hughes | |
| 6,322,519 B1 | 11/2001 | Moulin | |
| 7,063,669 B2 | 6/2006 | Brawner et al. | |
| 7,094,208 B2 | 8/2006 | Williams et al. | |
| 7,282,032 B2 | 10/2007 | Miller | |
| 2002/0151813 A1* | 10/2002 | Niles et al. ................... | 600/532 |
| 2007/0161901 A1* | 7/2007 | Takeda .................... | G01F 1/663 |
| | | | 600/455 |
| 2007/0261498 A1* | 11/2007 | Orr et al. ......................... | 73/753 |
| 2007/0273887 A1 | 11/2007 | Russell | |
| 2008/0000477 A1 | 1/2008 | Huster et al. | |

* cited by examiner

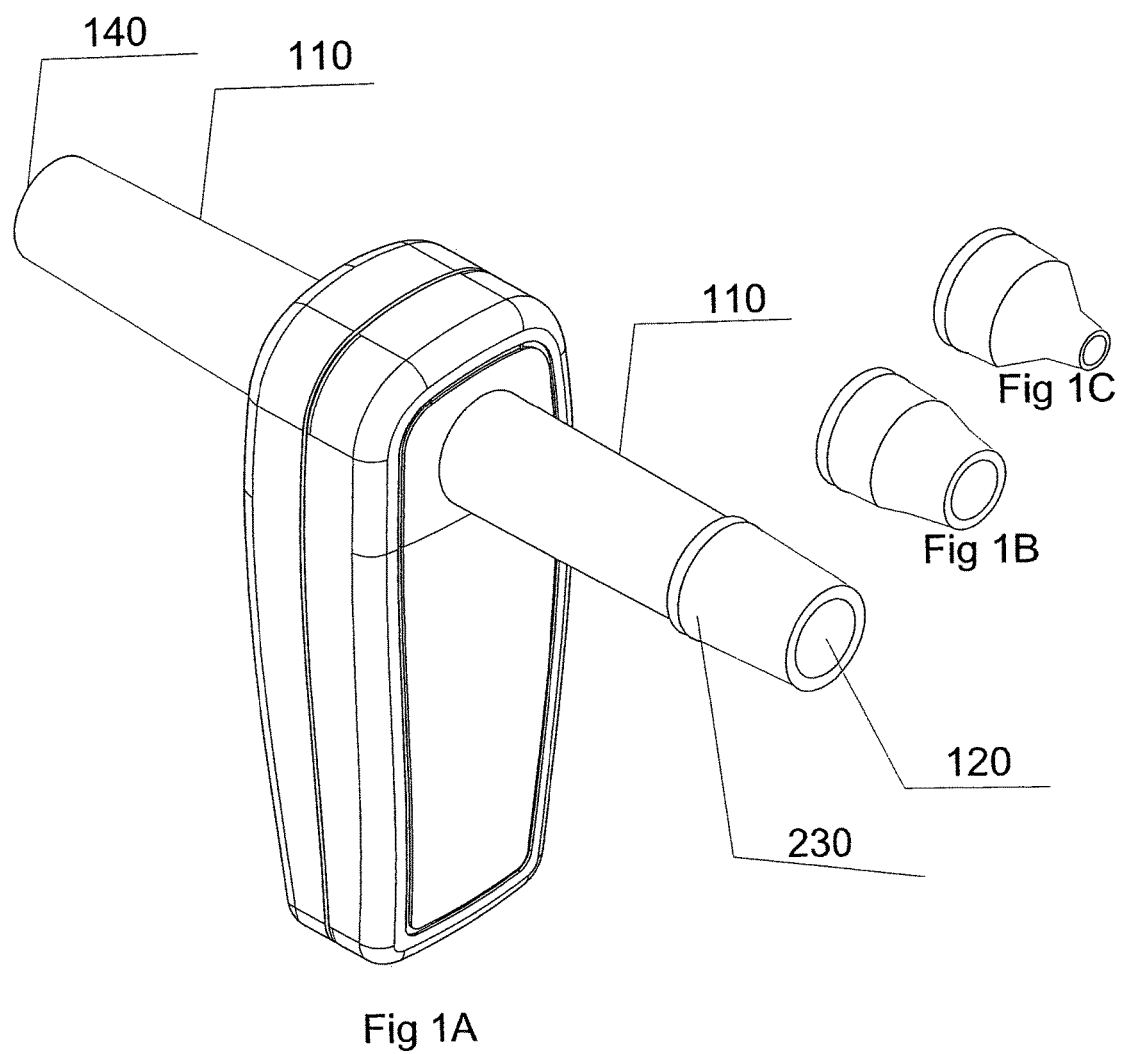

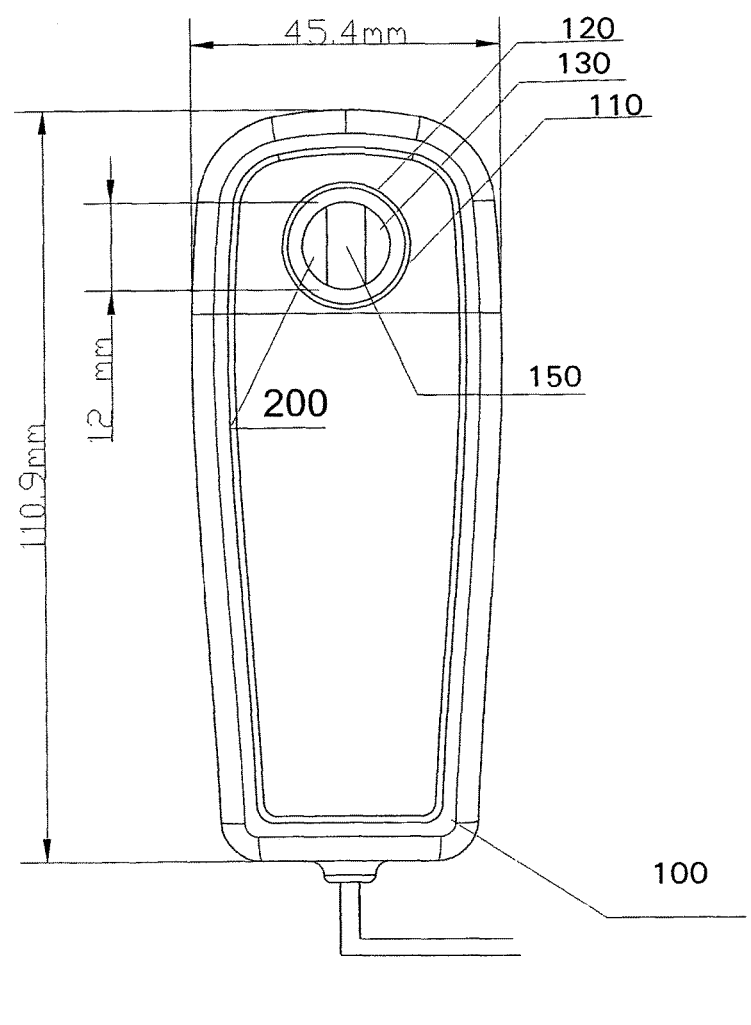

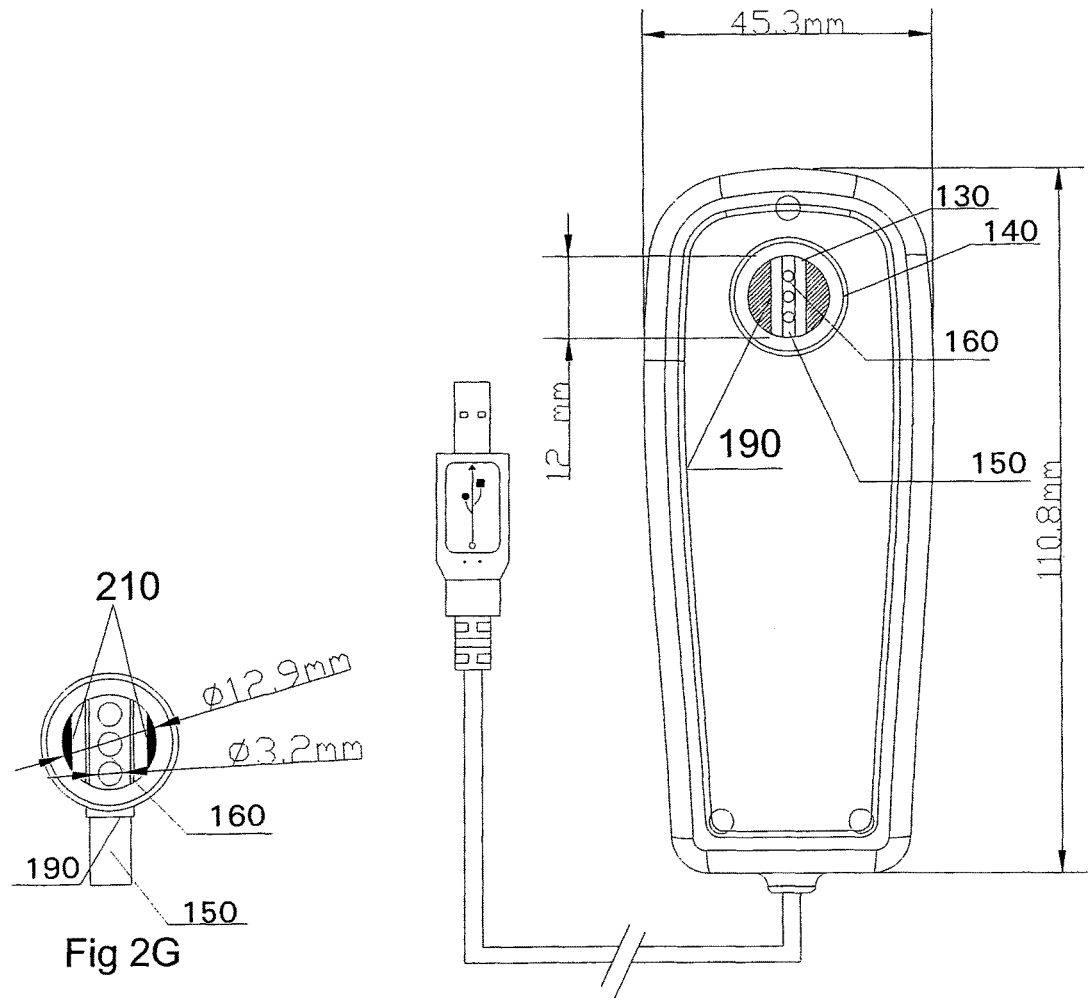

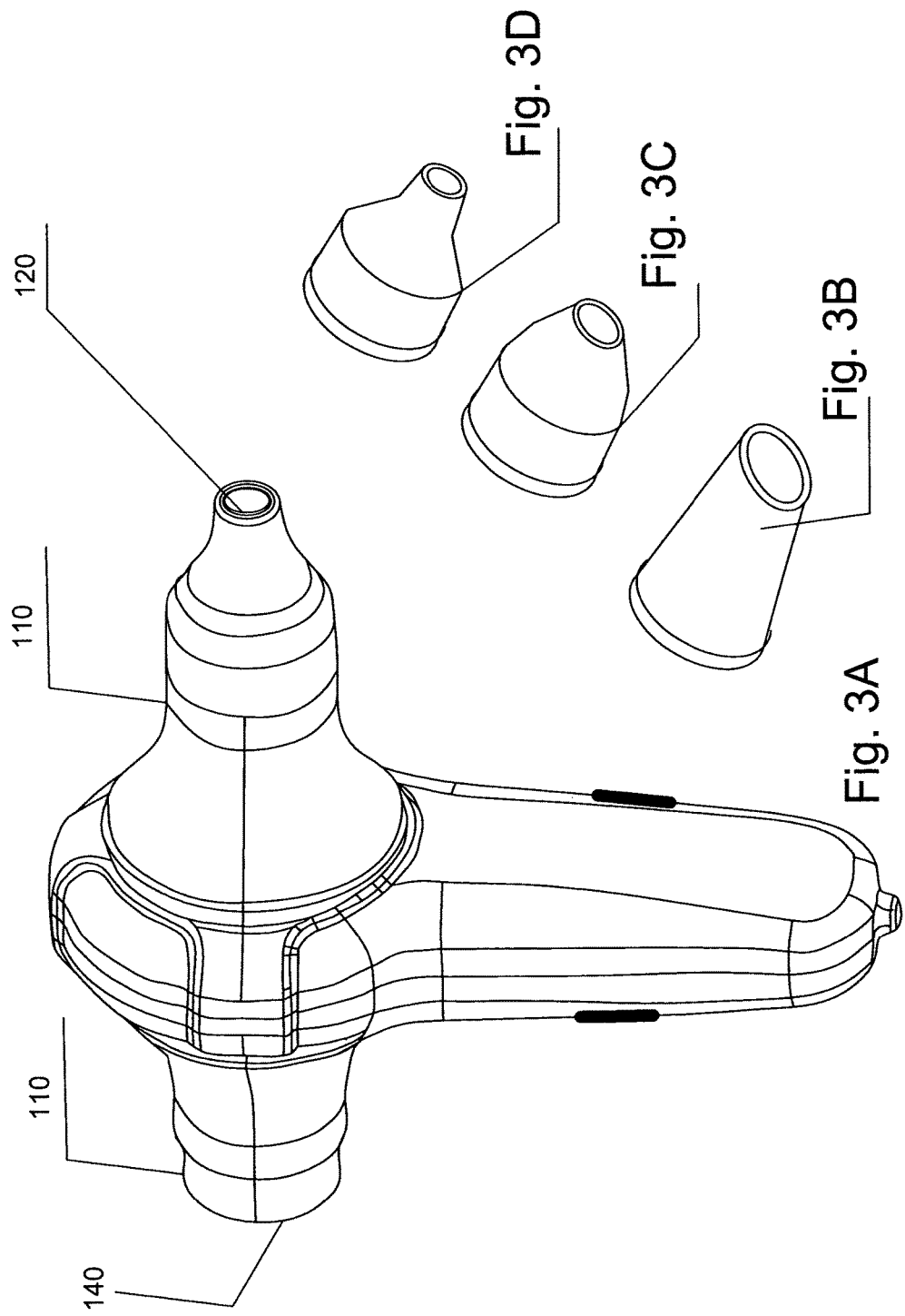

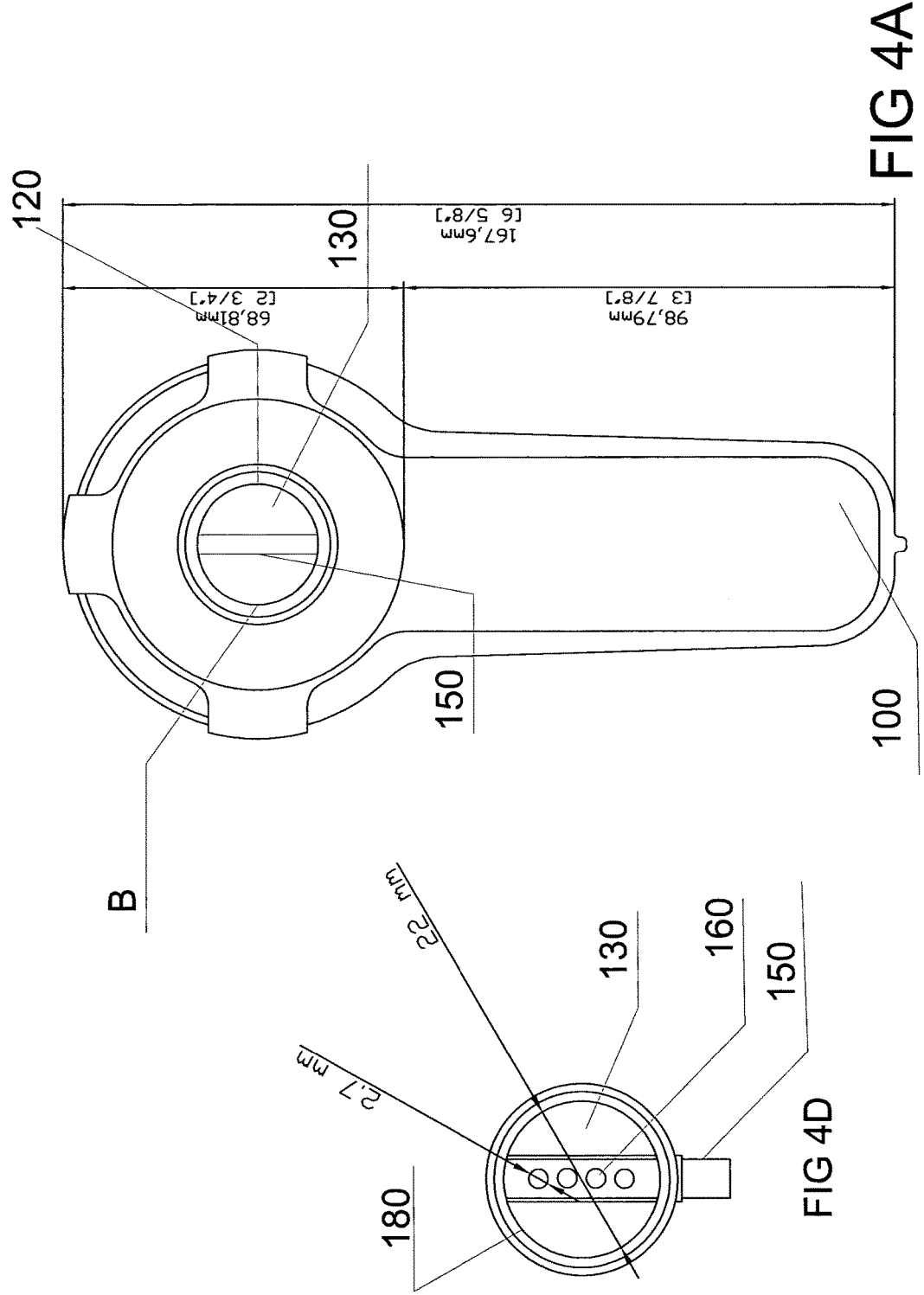

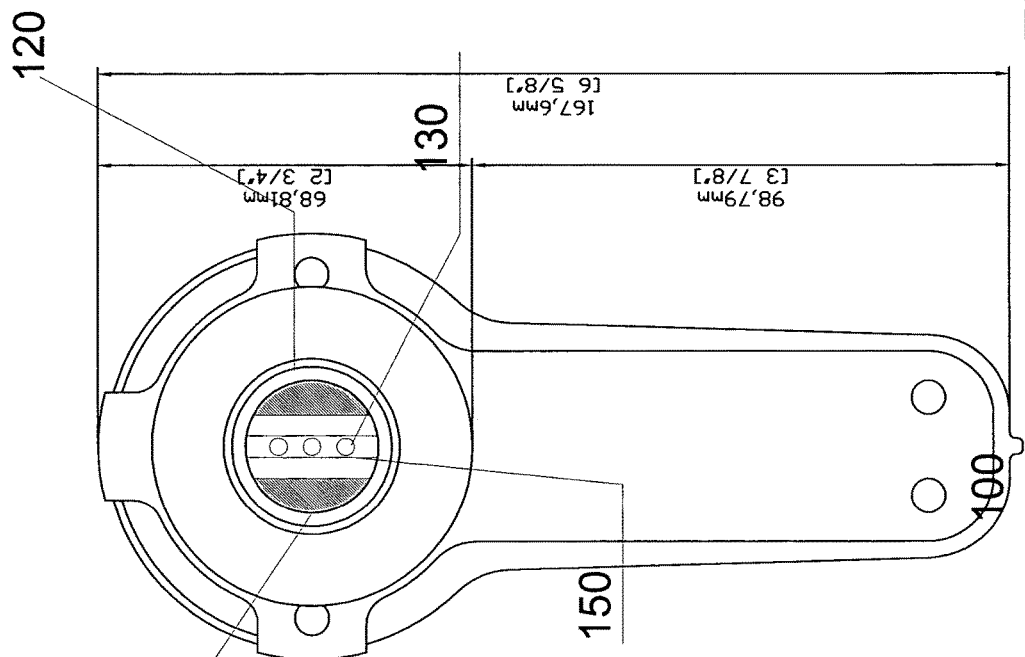
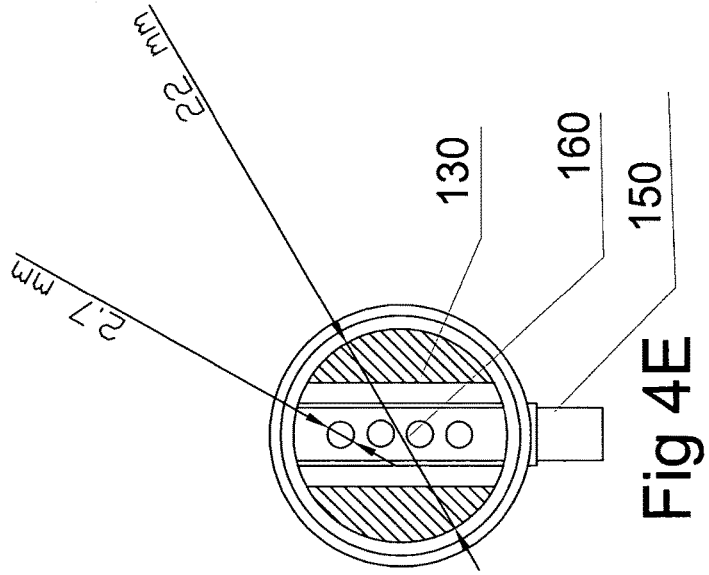

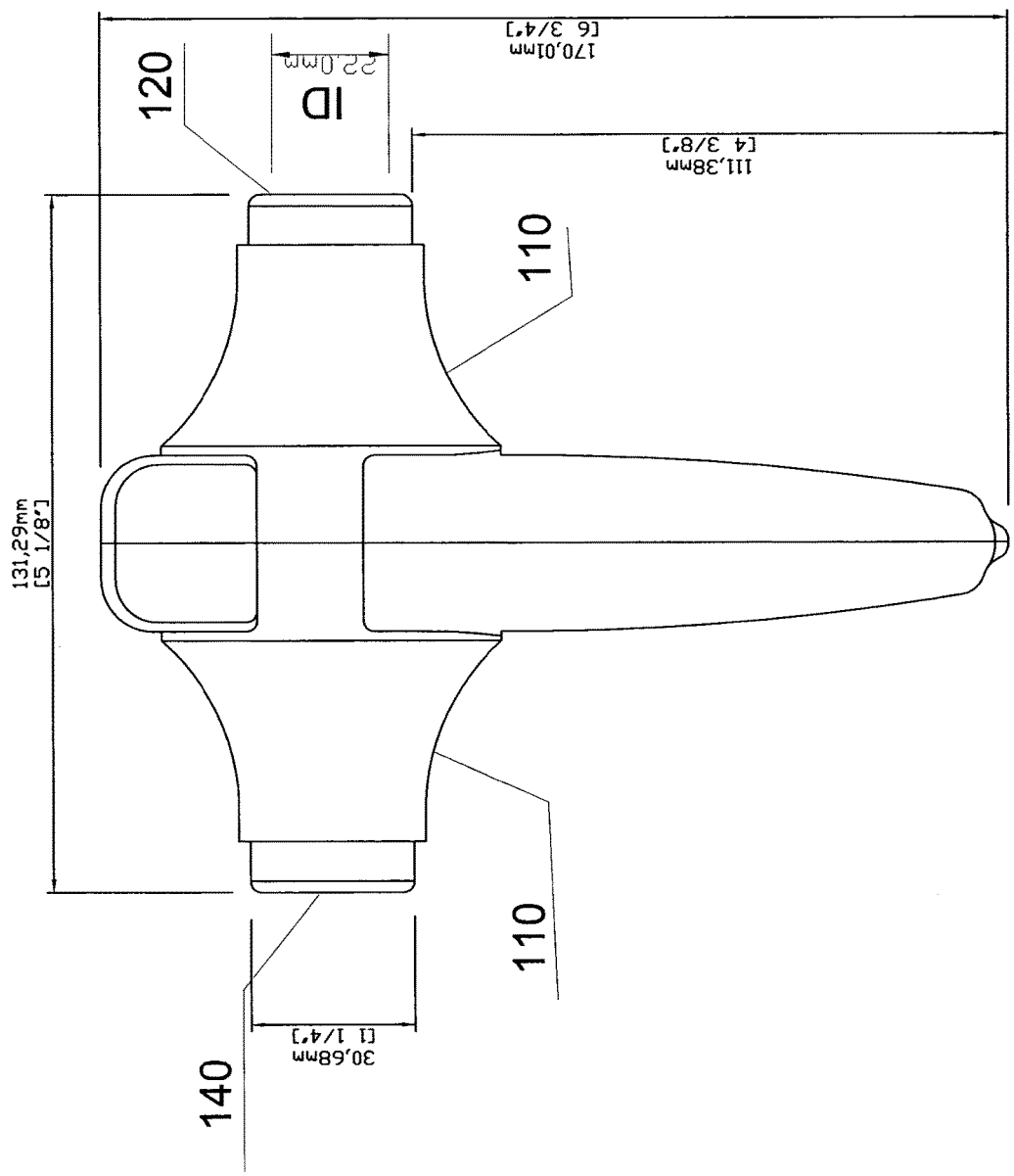

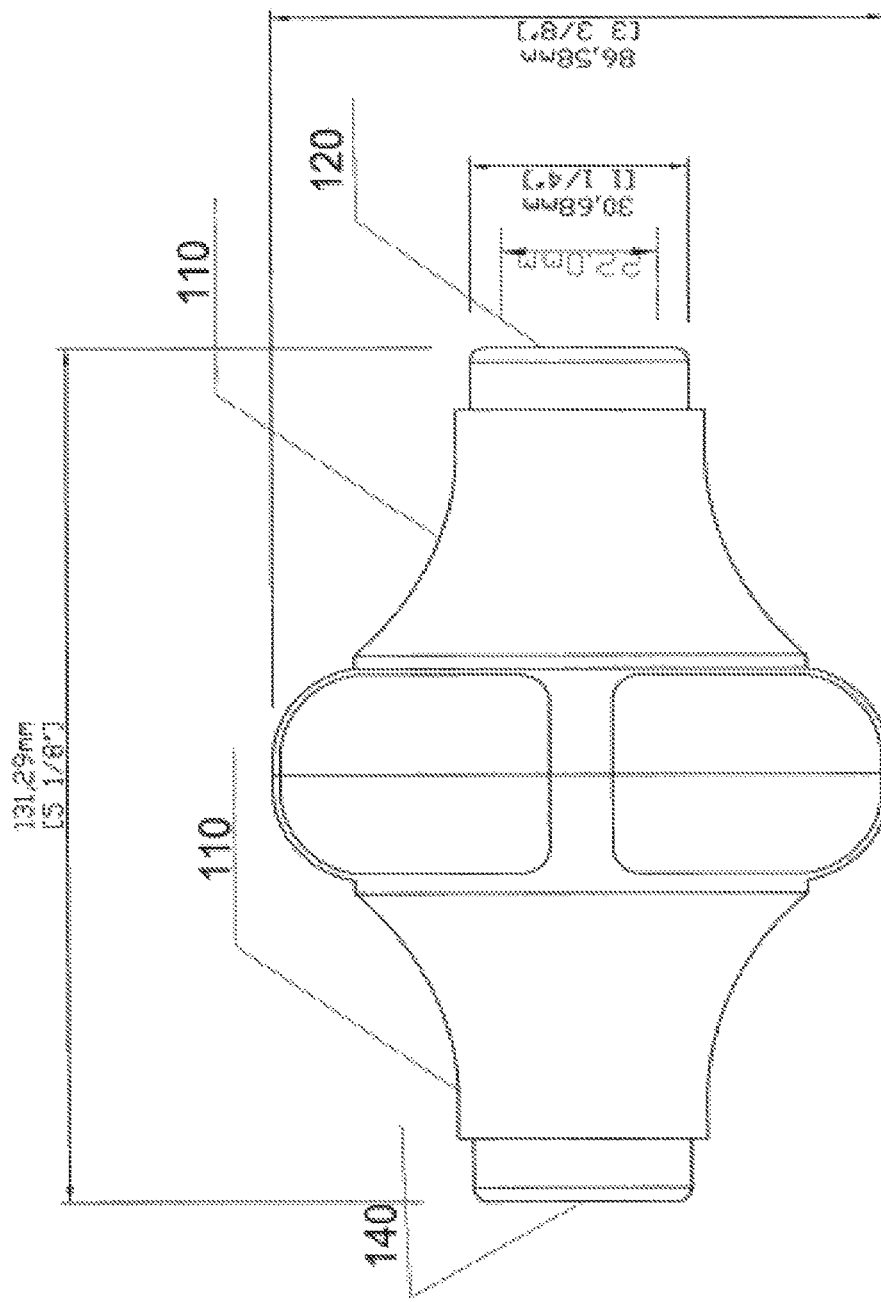

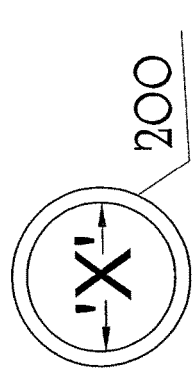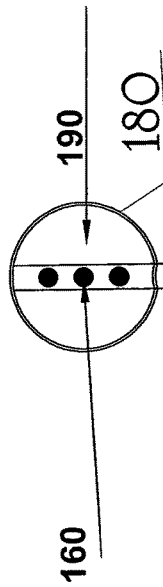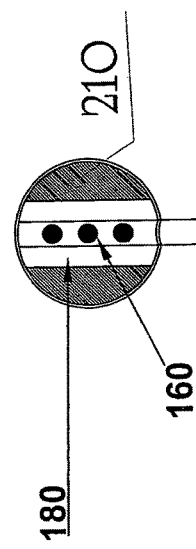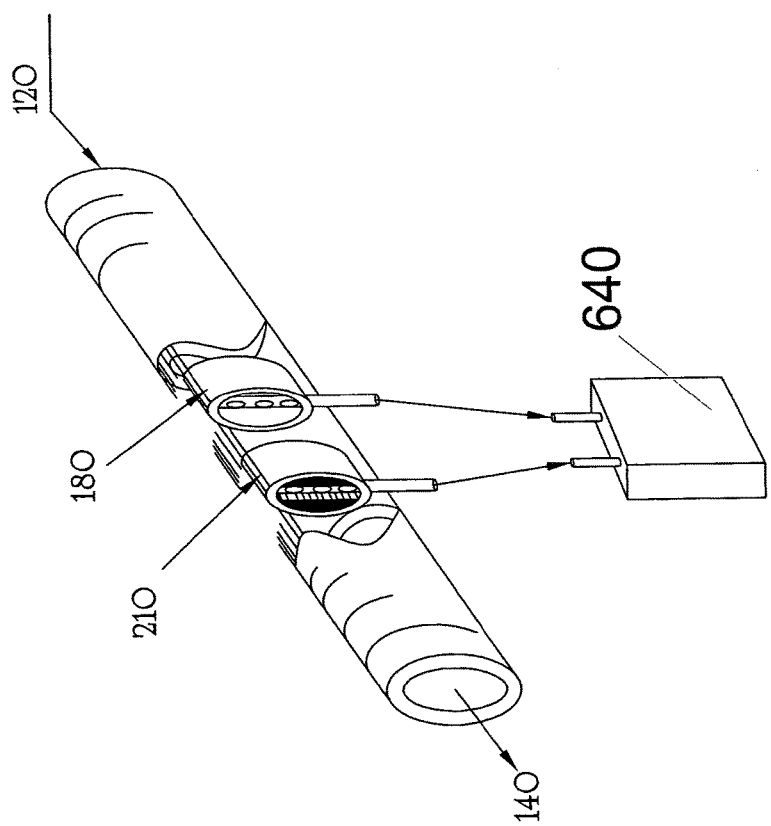

| A. Air Velocity | B. Area | C. Air velocity * Area Liters/second | D. Digital Output 0-1024 |
| --- | --- | --- | --- |
| 5.2 | 0.23 | 1.2 | 40 |
| 10.87 | 0.23 | 2.5 | 140 |
| 15.22 | 0.23 | 3.5 | 250 |
| 19.56 | 0.23 | 4.5 | 350 |
| 26.08 | 0.23 | 6.0 | 500 |
| 30.4 | 0.23 | 7.0 | 600 |
| 34.78 | 0.23 | 8.0 | 700 |
| 39.13 | 0.23 | 9.0 | 800 |
| 43.48 | 0.23 | 10.0 | 880 |
| 47.82 | 0.23 | 11.0 | 1000 |

SPIROMETER APPARATUS AND METHODS USEFUL IN CONJUNCTION THEREWITH

REFERENCE TO CO-PENDING APPLICATIONS

Priority is claimed from co-pending U.S. Ser. No. 61/233,681 filed on Aug. 13, 2009 and entitled "IMPROVED SPIROMETER APPARATUS AND METHODS USEFUL IN CONJUNCTION THEREWITH".

FIELD OF THE INVENTION

The present invention relates generally to spirometry and more particularly to spirometers which utilize the Venturi effect.

BACKGROUND OF THE INVENTION

The Venturi effect is the reduction in fluid pressure that results when a fluid flows through a constricted section of pipe. Venturi masks are used in the medical administration of oxygen. Venturi tubes, also termed "venturis", are used to measure the speed of a fluid, by measuring pressure changes at different segments of the device. When fluid flows though a Venturi the pressure in the two ends of the tube will differ, directing the fluid to the "low pressure" portion of the tube. The amount of motion can be calibrated to the speed of the fluid flow.

According to Wikipedia, "spirometry (meaning the measuring of breath) is the most common of the Pulmonary Function Tests (PFTs), measuring lung function, specifically the measurement of the amount (volume) and/or speed (flow) of air that can be inhaled and exhaled.

"Most spirometers display the following graphs, called spirograms:

a volume-time curve, showing volume (liters) along the Y-axis and time (seconds) along the X-axis a flow-volume loop, which graphically depicts the rate of airflow on the Y-axis and the total volume inspired or expired on the X-axis "Generally, the patient is asked to take the deepest breath they can, and then exhale into the sensor as hard as possible, for as long as possible. It is sometimes directly followed by a rapid inhalation (inspiration), in particular when assessing possible upper airway obstruction. Sometimes, the test will be preceded by a period of quiet breathing in and out from the sensor (tidal volume), or the rapid breath in (forced inspiratory part) will come before the forced exhalation."

Wikipedia explains that the following results are often generated in spirometric tests:

Results often generated in spirometric tests

| Abbreviation | Name | Description |
| --- | --- | --- |
| FVC | Forced Vital Capacity | total amount of air that can be forcibly be blown out after full inspiration, measured in liters. |
| $FEV_1$ | Forced Expiratory Volume in 1 Second | amount of air that subject can forcibly blow out in one second, measured in liters. Along with FVC it is considered one of the primary indicators of lung function. |
| $FEV_1$/FVC | FEV1% | ratio of $FEV_1$ to FVC. In healthy adults this should be approximately 75-80%. |
| PEF | Peak Expiratory Flow | speed of the air moving out of your lungs at the beginning of the expiration, measured in liters per second. |
| FEF | Forced | average flow (or speed) of air coming out of |

Results often generated in spirometric tests

| Abbreviation | Name | Description |
| --- | --- | --- |
| 25-75% or 25-50% | Expiratory Flow 25-75% or 25-50% | the lung during the middle portion of the expiration (also sometimes referred to as the MMEF, for maximal mid-expiratory flow). |
| FIF 25-75% or 25-50% | Forced Inspiratory Flow 25-75% or 25-50% | similar to FEF 25-75% or 25-50% except the measurement is taken during inspiration. |
| FET | Forced Expiratory Time | measures the length of the expiration in seconds. |
| SVC | Slow Vital Capacity | Maximum volume of air that can be exhaled slowly after slow maximum inhalation. |
| TV | Tidal volume | During the respiratory cycle, a specific volume of air is drawn into and then expired out of the lungs. This volume is tidal volume. |
| MVV | Maximum Voluntary Ventilation | A measure of the maximum amount of air Voluntary that can be inhaled and exhaled in one minute, measured in liters/minute. |

Spirometry requires patient cooperation hence is normally repeated at least three times to ensure reproducibility. Certain spirometry results can be underestimated but never overestimated. Conventional technology pertaining to certain embodiments of the present invention is described in the following publications inter alia: U.S. Pat. No. 7,282,032 to Miller, U.S. Pat. No. 7,094,208 to Williams et al, and U.S. Pat. No. 7,063,669 to Brawner et al.

The disclosures of all publications and patent documents mentioned in the specification, and of the publications and patent documents cited therein directly or indirectly, are hereby incorporated by reference.

SUMMARY OF THE INVENTION

A spirometer may be the only apparatus that can detect and warn about COPD illness 10-12 years before an individual would reach a critical point of no return and will need oxygen supply and equipment to sustain minimal breathing.

Certain embodiments of the present invention seek to provide improved spirometer apparatus which may be used in conjunction with inhalation-exhalation training software. The apparatus shown and described herein may be usable at a variety of settings such as a doctor's office, hospital or home. Typically, the apparatus shown and described herein facilitates both inhalation and exhalation using a single device.

The apparatus may include a primary blowing tube which guides incoming air toward vertical tubes positioned in a series type configuration, such as two such tubes. The vertical tubes may have multiple holes disposed opposite the blown-in incoming air side and may be connected to a differential pressure sensor. The primary tube has an internal surface whose cross-sectional dimension typically decreases at the location of the second vertical tube. The speed and power of the blown-in air therefore increase. The outgoing air creates a low pressure by sucking air outward at the reverse flow, all in accordance with Venturi's Law. The pressures inside each of the vertical tubes may be measured by the differential pressure sensor, and may be magnified and suitably calibrated to provide an output of a blowing user's air quantity (e.g. in liters) and blowing power (e.g. in liters/second).

Reduction of the cross-sectional dimension along the length of the primary tube may be provided so as to generate magnified static pressure in comparison to the initial incoming pressure (which may be measured at the first vertical tube) due to the narrowing of the air path.

Typically, air is sucked or inhaled on the same side of the Primary tube that it is exhaled. There is thus provided, in accordance with at least one embodiment of the present invention, spirometer apparatus comprising a main vessel defining a main volume and including an air inputting and outputting mouthpiece at a first end thereof and an air inlet/outlet at a second end thereof; first and second internal vessels defining first and second internal volumes respectively within the main volume, the first internal vessel being closer to the mouthpiece than the second, wherein the cross-section of the main volume adjacent the second internal volume is less than the cross-section of the main volume adjacent the first internal volume, wherein the first and second internal volumes have fluid communication with the main volume via at least one first internal vessel opening and at least one second internal vessel opening respectively, the fluid communication between the main volume and the second internal volume being provided solely via the at least one second internal vessel opening, and wherein the at least one second internal vessel opening is not located along the path of air exhaled from the mouthpiece such that the at least one second internal vessel opening faces onto air moving from the second internal volume toward the inlet/outlet of the main vessel; and a pressure sensor operative to measure an air pressure differential between the two internal volumes.

Further in accordance with at least one embodiment of the present invention, the distance between the first and second internal volumes is relatively small such that the first internal vessel opening is located within a high-pressure area within the main volume generated adjacent the lesser cross section adjacent the second internal volume.

Still further in accordance with at least one embodiment of the present invention, the main vessel comprises an elongate member having a diameter and the first and second internal volumes are located a distance d away from the first and second ends of the elongate member respectively, the distance d equaling typically at least three times the diameter.

Additionally in accordance with at least one embodiment of the present invention, the first internal vessel openings are not located along the path of air exhaled from the mouthpiece.

Further in accordance with at least one embodiment of the present invention, each of the vessels comprises a tube.

Still further in accordance with at least one embodiment of the present invention, the first and second internal vessels have first and second external cross-sections respectively, the main vessel having first and second internal cross-sections adjacent the first and second internal vessels respectively, wherein the first external cross-section is smaller than the first internal cross-section, the second external cross-section is smaller than the second internal cross-section, and wherein the second external cross-section is smaller than the first external cross-section, thereby to cause a pressure drop between the first and second internal vessels during inhale and during exhale.

Additionally in accordance with at least one embodiment of the present invention, at least one tube is circular in cross-section.

Further in accordance with at least one embodiment of the present invention, the internal vessels comprise tubes which are mutually parallel.

Still further in accordance with at least one embodiment of the present invention, the internal vessels comprise tubes which are perpendicular to the main vessel.

Yet further in accordance with at least one embodiment of the present invention, the at least one opening comprises a plurality of openings.

Further in accordance with at least one embodiment of the present invention, the plurality of openings comprises 3 openings.

Still further in accordance with at least one embodiment of the present invention, the plurality of openings is evenly spaced.

Additionally in accordance with at least one embodiment of the present invention, the second cross-section is a rectangular cross section including having a first longer dimension and a second shorter dimension and wherein the at least one opening comprises a plurality of openings arranged along the first longer dimension.

Further in accordance with at least one embodiment of the present invention, the apparatus also comprises respiration training software for which the sensor provides feedback.

Still further in accordance with at least one embodiment of the present invention, the internal vessels divide the cross-section of the main vessel into two.

Additionally in accordance with at least one embodiment of the present invention, each of the internal vessels includes a first open end communicating with the differential pressure sensor and a second sealed end.

Also provided, in accordance with at least one embodiment of the present invention, is a spirometry method comprising providing a main vessel defining a main volume and including an air inputting and outputting mouthpiece at a first end thereof and an air inlet/outlet at a second end thereof; providing first and second internal vessels defining first and second internal volumes respectively within the main volume, the first internal vessel being closer to the mouthpiece than the second, wherein the cross-section of the main volume adjacent the second internal volume is less than the cross-section of the main volume adjacent the first internal volume, wherein the first and second internal volumes have fluid communication with the main volume via at least one first internal vessel opening and at least one second internal vessel opening respectively, the fluid communication between the main volume and the second internal volume being provided solely via the at least one second internal vessel opening, and wherein the at least one second internal vessel opening is not located along the path of air exhaled from the mouthpiece such that the at least one second internal vessel opening faces onto air moving from the second internal volume toward the inlet/outlet of the main vessel; and using a pressure sensor to measure an air pressure differential between the two internal volumes.

Further in accordance with at least one embodiment of the present invention, the method also comprises using the air pressure differential as feedback for respiration training.

According to certain embodiments of the present invention, spirometer apparatus is provided having an air inputting and outputting mouthpiece at a first end thereof and an air inlet/outlet at a second end thereof. First and second internal volumes are defined within the main volume of the spirometer and have fluid communication therewith, via at least one first internal volume opening and at least one second internal volume opening respectively, the first internal volume being closer to the mouthpiece than the second.

The fluid communication between the main volume and the second internal volume is provided solely via at least one second internal volume opening which is not located along the path of air exhaled from the mouthpiece such that the at least one second internal volume opening faces the air moving from the vicinity of the second internal volume toward the inlet/outlet of the main volume. The cross-section of the main volume adjacent the second internal volume is less than the cross-section of the main volume adjacent the first internal volume. An air pressure differential is generated between the two internal volumes and is typically measured by a conventional differential pressure sensor whose two sensing ends communicate with the two internal volumes respectively. Specifically, when air is exhaled by a human subject through the mouthpiece and into the spirometer, eventually exiting the air inlet/outlet, the air pressure at the first internal volume exceeds that at the second internal volume. When air is inhaled by a human subject from the spirometer outward through the mouthpiece, causing an influx of air from the inlet/outlet into the main volume of the spirometer, the air pressure at the second internal volume exceeds that at the first internal volume.

As exhaled air approaches the lesser cross section adjacent the second internal volume, its pressure rises generating a high-pressure area. Preferably, the distance between the first and second internal volumes is relatively small such that the first internal volume outlet is located within the high-pressure area.

Typically, the main volume comprises an elongate member having a diameter and the first and second internal volumes are located a significant distance away from each of the two ends of the elongate member, the distance typically at least three times the diameter, e.g. in order to ensure that the air flow through the elongate member is generally parallel to the axis of the elongate member, hence enhance uniformity of pressure differential measurements and/or in order to prevent tampering with the functional units of the spirometer.

Typically, the first internal volume openings are not located along the path of air exhaled from the mouthpiece.

Also provided is a computer program product, comprising a computer usable medium or computer readable storage medium, typically tangible, having a computer readable program code embodied therein, the computer readable program code adapted to be executed to implement any or all of the methods shown and described herein. It is appreciated that any or all of the computational steps shown and described herein may be computer-implemented. The operations in accordance with the teachings herein may be performed by a computer specially constructed for the desired purposes or by a general purpose computer specially configured for the desired purpose by a computer program stored in a computer readable storage medium.

Any suitable processor, display and input means may be used to process, display e.g. on a computer screen or other computer output device, store, and accept information such as information used by or generated by any of the methods and apparatus shown and described herein; the above processor, display and input means including computer programs, in accordance with some or all of the embodiments of the present invention. Any or all functionalities of the invention shown and described herein may be performed by a conventional personal computer processor, workstation or other programmable device or computer or electronic computing device, either general-purpose or specifically constructed, used for processing; a computer display screen and/or printer and/or speaker for displaying; machine-readable memory such as optical disks, CDROMs, magnetic-optical discs or other discs; RAMs, ROMs, EPROMs, EEPROMs, magnetic or optical or other cards, for storing, and keyboard or mouse for accepting. The term "process" as used above is intended to include any type of computation or manipulation or transformation of data represented as physical, e.g. electronic, phenomena which may occur or reside e.g. within registers and/or memories of a computer.

The above devices may communicate via any conventional wired or wireless digital communication means, e.g. via a wired or cellular telephone network or a computer network such as the Internet.

The apparatus of the present invention may include, according to certain embodiments of the invention, machine readable memory containing or otherwise storing a program of instructions which, when executed by the machine, implements some or all of the apparatus, methods, features and functionalities of the invention shown and described herein. Alternatively or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention. Any of the teachings incorporated herein may, wherever suitable, operate on signals representative of physical objects or substances.

The embodiments referred to above, and other embodiments, are described in detail in the next section.

Any trademark occurring in the text or drawings is the property of its owner and occurs herein merely to explain or illustrate one example of how an embodiment of the invention may be implemented.

Unless specifically stated otherwise, as apparent from the following discussions, it is appreciated that throughout the specification discussions, utilizing terms such as, "processing", "computing", "estimating", "selecting", "ranking", "grading", "calculating", "determining", "generating", "reassessing", "classifying", "generating", "producing", "stereo-matching", "registering", "detecting", "associating", "superimposing", "obtaining" or the like, refer to the action and/or processes of a computer or computing system, or processor or similar electronic computing device, that manipulate and/or transform data represented as physical, such as electronic, quantities within the computing system's registers and/or memories, into other data similarly represented as physical quantities within the computing system's memories, registers or other such information storage, transmission or display devices. The term "computer" should be broadly construed to cover any kind of electronic device with data processing capabilities, including, by way of non-limiting example, personal computers, servers, computing system, communication devices, processors (e.g. digital signal processor (DSP), microcontrollers, field programmable gate array (FPGA), application specific integrated circuit (ASIC), etc.) and other electronic computing devices.

The present invention may be described, merely for clarity, in terms of terminology specific to particular programming languages, operating systems, browsers, system versions, individual products, and the like. It will be appreciated that this terminology is intended to convey general principles of operation clearly and briefly, by way of example, and is not intended to limit the scope of the invention to any particular programming language, operating system, browser, system version, or individual product.

BRIEF DESCRIPTION OF THE DRAWINGS

Certain embodiments of the present invention are illustrated in the following drawings:

FIG. 1A is an isometric view of spirometer apparatus constructed and operative in accordance with a first embodiment of the present invention.

FIGS. 1B and 1C are alternative configurations for the mouthpiece of FIG. 1A.

FIGS. 2A-2E are front, rear, side, top and bottom views of the apparatus of FIG. 1A.

FIG. 2F illustrates a pair of rings that may be employed to hold the vertical tubes 150 of FIG. 2A, in place.

FIG. 2G is an internal ring with multiple apertures provided in accordance with certain embodiments of the present invention and operative to guide reverse pressure to the Pressure sensor shown and described herein, typically along a vertical axis.

FIG. 3A is an isometric view of spirometer apparatus constructed and operative in accordance with a second embodiment of the present invention.

FIGS. 3B, 3C and 3D are alternative configurations for the mouthpiece of FIG. 3A.

FIGS. 4A-4C are front, rear and side views of the apparatus of FIG. 1A.

FIG. 4E is an enlarged view of the internal chamber C in FIG. 4B which is partially blocked to generate narrow openings.

FIG. 4F is a top view of the apparatus of FIG. 1A.

FIG. 5B illustrates a suitable interaction between the spirometry apparatus shown and described above and the pressure sensor of FIG. 5A.

FIGS. 5C-5E are cross-sectional front and reverse views of the spirometry apparatus of FIG. 5B.

FIG. 7 is an example of a digital output vs. air velocity table generated by the system of FIG. 6B.

DETAILED DESCRIPTION OF CERTAIN EMBODIMENTS

Figure 2C:
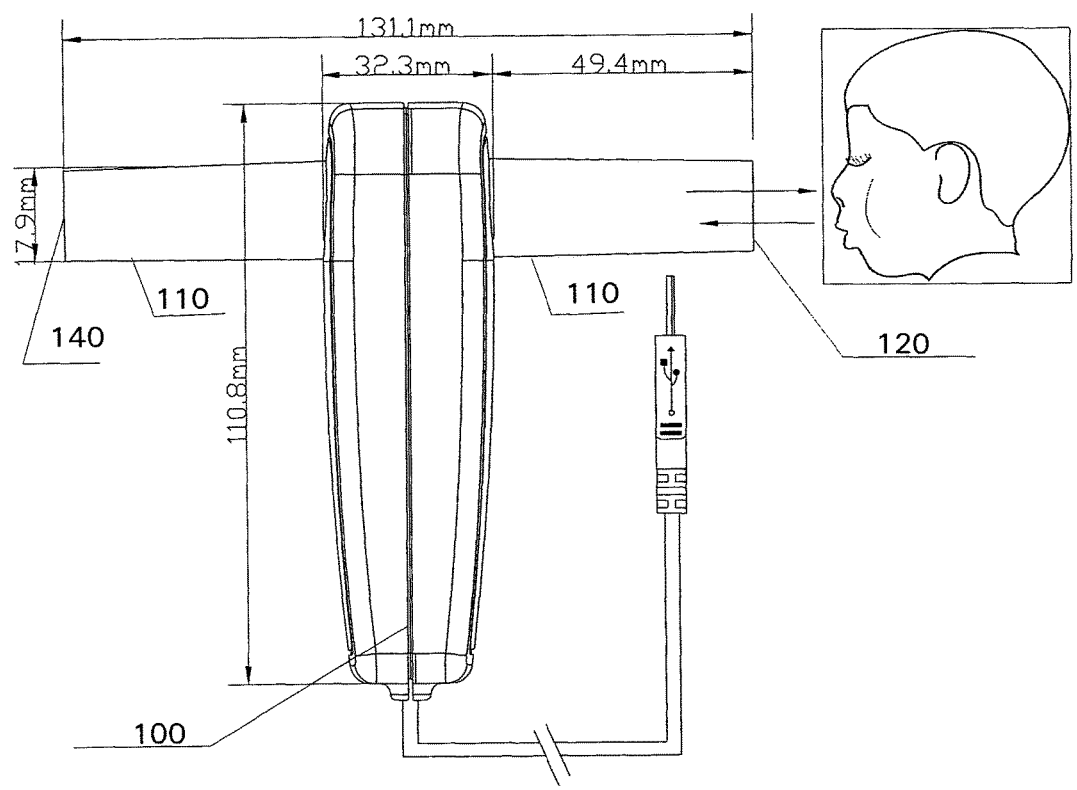

FIGS. 1A-2G illustrate spirometer apparatus constructed and operative in accordance with a first embodiment of the present invention. FIGS. 3A-4F illustrate spirometer apparatus constructed and operative in accordance with a first embodiment of the present invention. The common features of the two embodiments are now described. The spirometer apparatus 100 of FIGS. 2A-4F includes a main inhale-exhale tube 110 having a first end 120 into which a patient inhales and exhales, a main interior 130, and a second open end 140. A plurality of smaller intersecting tubes 150 intersect the main-inhale exhale tube 110 at first and second respective locations therealong and have a plurality of smaller interiors respectively. The first location is closer to the first end than is the second location. Each of the interiors of the tubes 150 are in fluid communication with the main interior 130 solely via at least one aperture 160 (e.g. 3 apertures 160 evenly spaced along the main tube, in the illustrated embodiment or 4 apertures in FIG. 4D) formed in each of the intersecting tubes 150 at locations facing the second end. The intersecting tubes 150 have first and second external cross-sections 180 and 190 respectively at the first and second locations respectively.

The main tube 110 has first and second internal cross-sections 200 and 210 respectively at the first and second respective locations respectively. As shown, the first external cross-section 180 is smaller than the first internal cross-section 200 and the second external cross-section 190 is smaller than the second internal cross-section 210. The second external cross-section 190 is smaller than the first external cross-section 180, thereby to cause a pressure drop between the first and second locations during inhale and during exhale. A differential pressure sensor 640 senses the pressure drop during inhale and during exhale. Each of the intersecting tubes 150 includes a first open end communicating with the differential pressure sensor and a second sealed end.

Figure 3E:
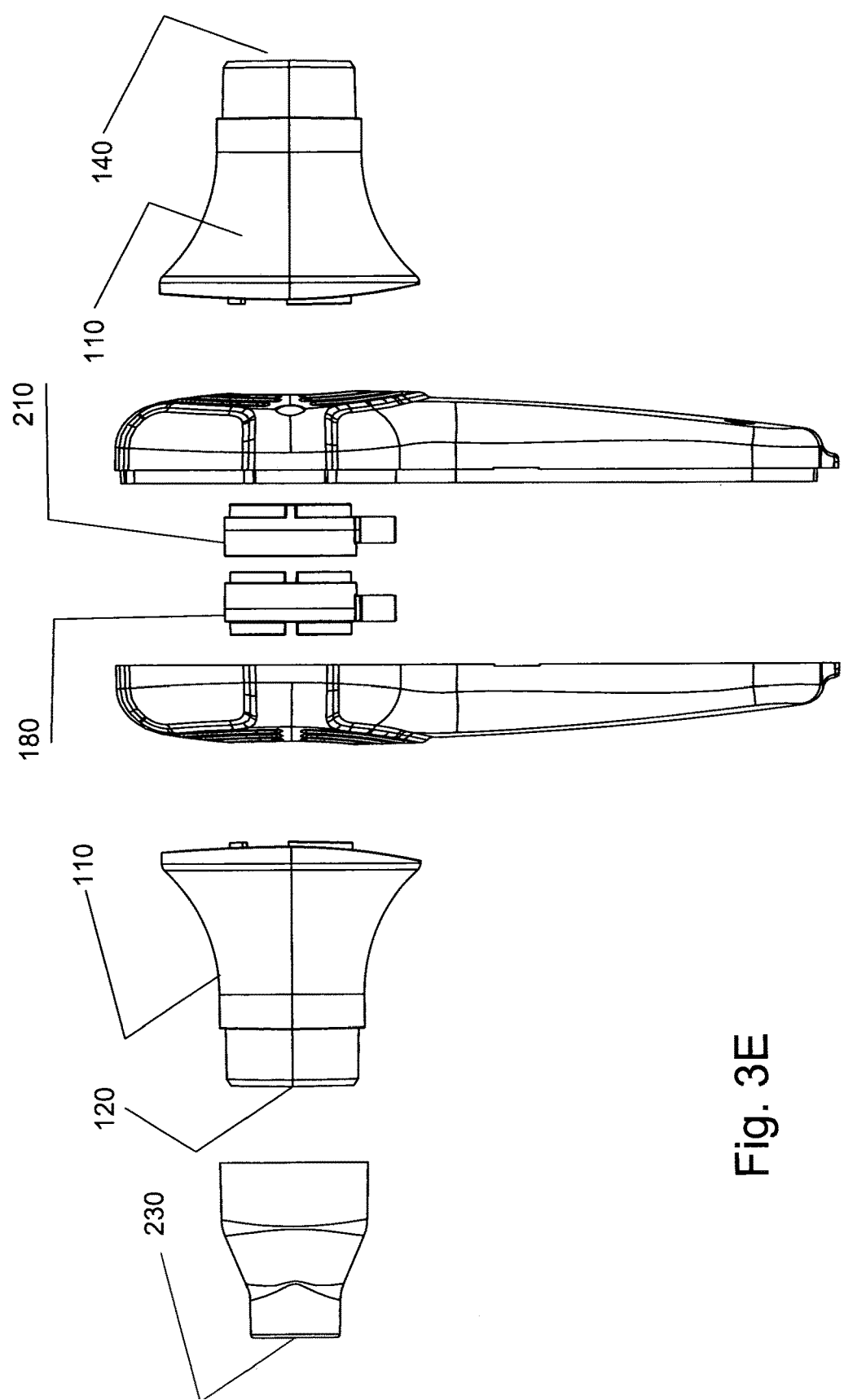
FIG. 3E is a side exploded view of the spirometer apparatus of FIG. 3A.
Figure 3F:
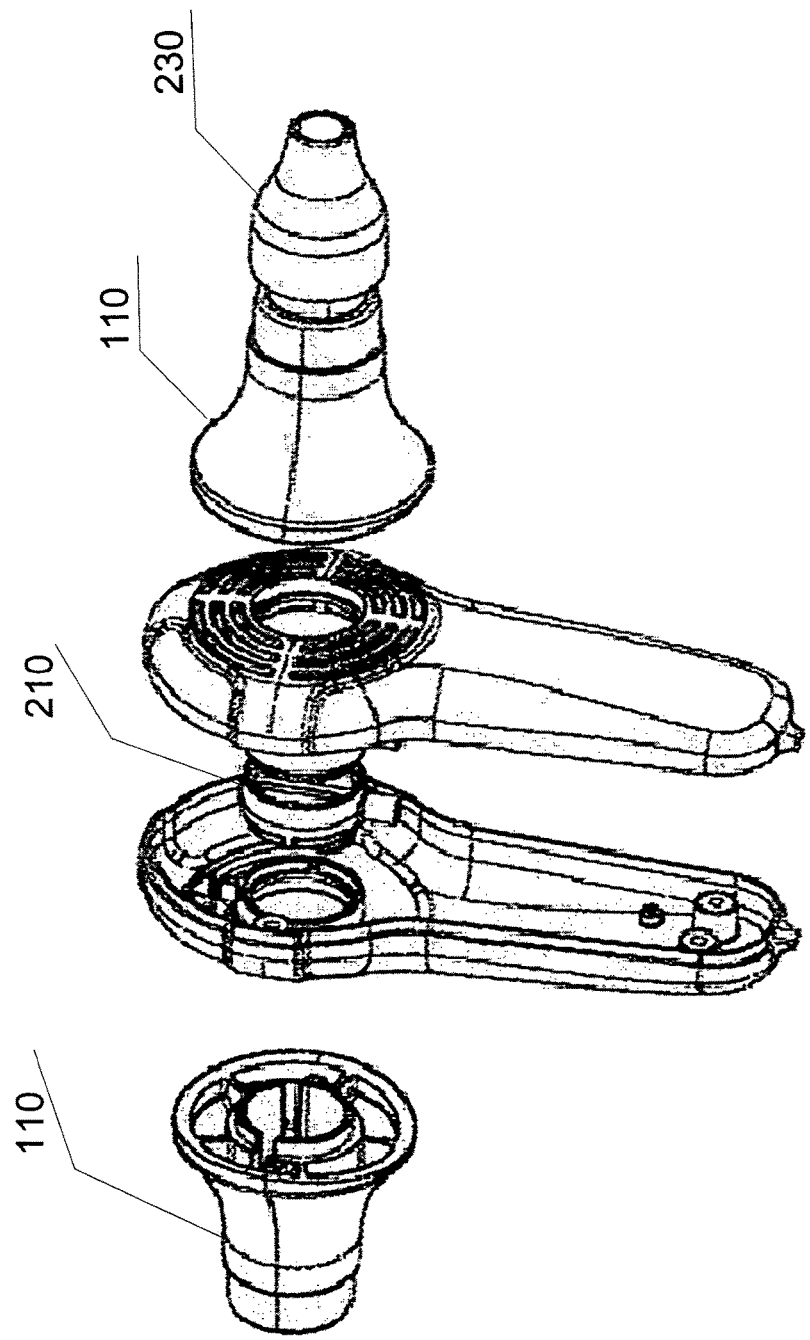
FIG. 3F is a perspective exploded view of the spirometer apparatus of FIG. 3A.
Figure 3G:
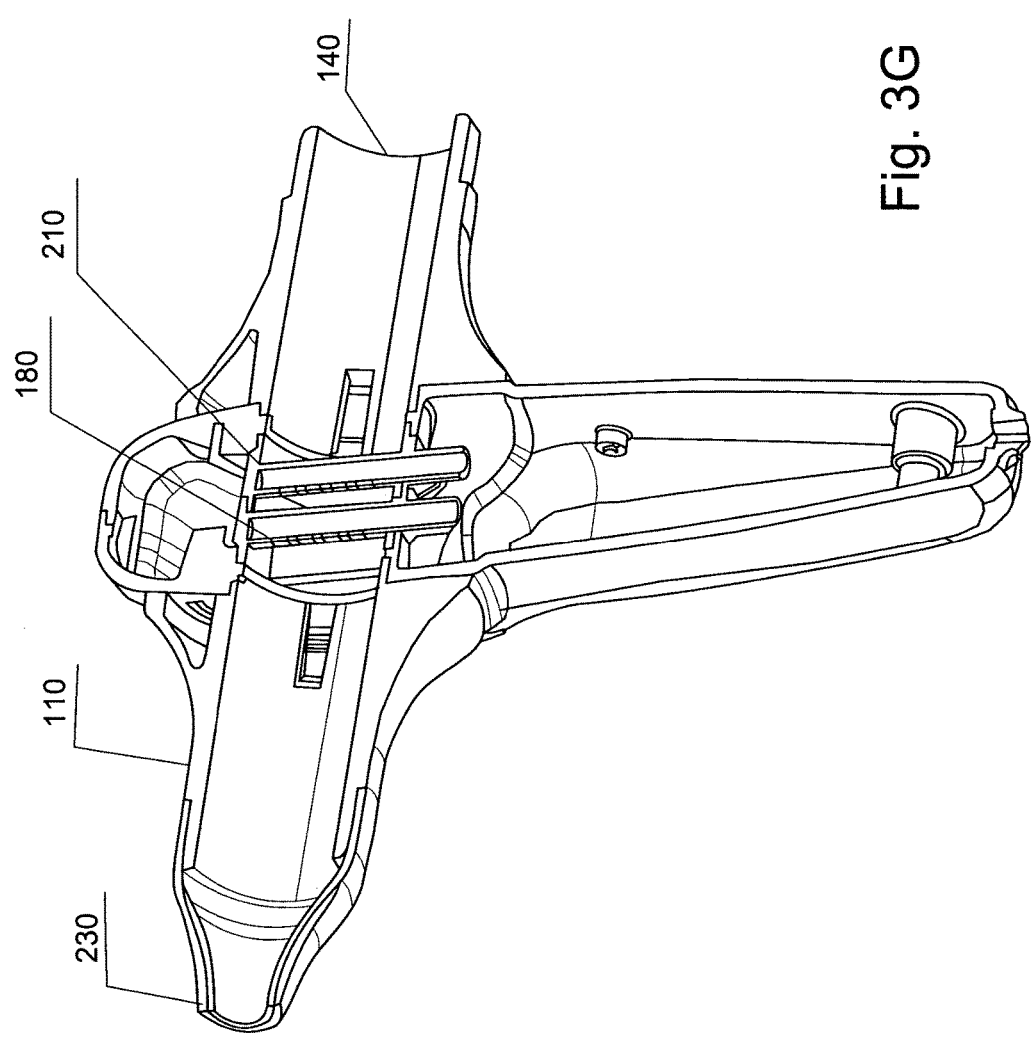
FIG. 3G is a cut-away perspective view of the apparatus of FIG. 3A.
Figure 4D:
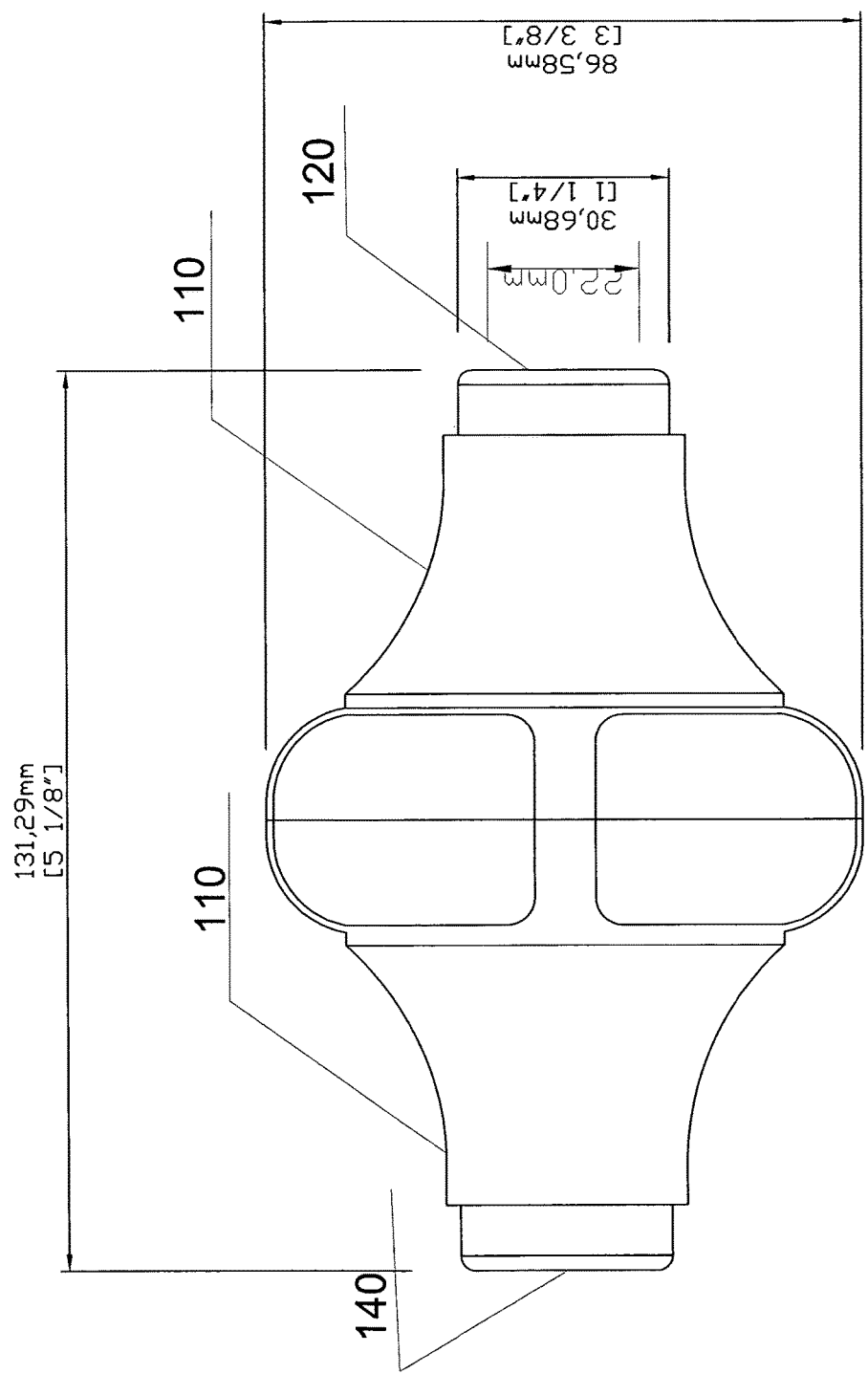
FIG. 4D is an enlarged back view of the internal chamber B of FIG. 4A.

It is appreciated that the mouthpiece 230 of FIGS. 1A and 3A may be selectably removable and replaceable, particularly in apparatus intended for use in a facility which serves multiple patients.

It is appreciated that the example dimensions shown in various of the drawings merely exemplify one possible implementation among a near-infinite set of possible implementations and one example of suitable relationships between the many parameters; the example dimensions are in no way intended to be limiting.

Figure 2D:
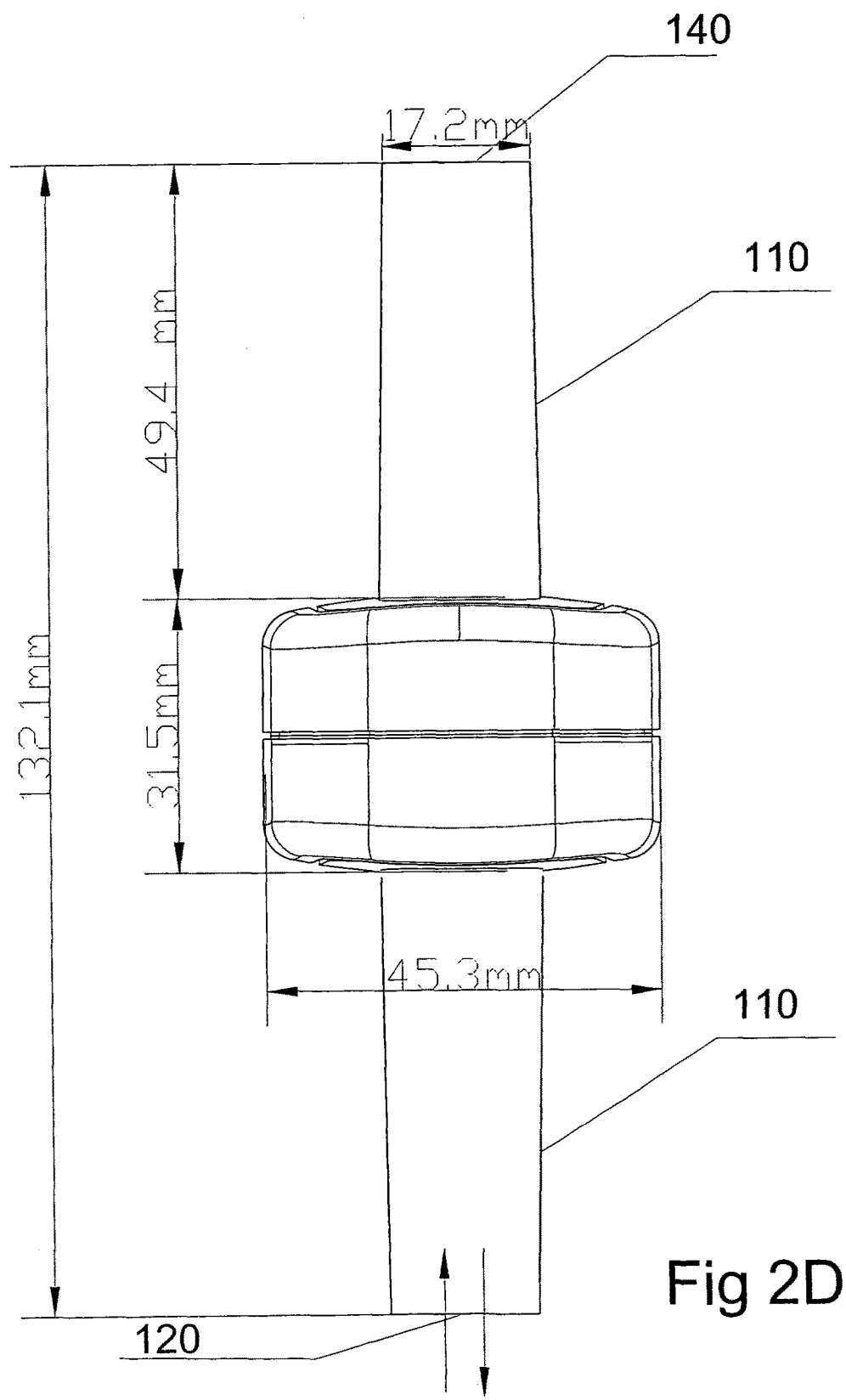
Figure 2E:
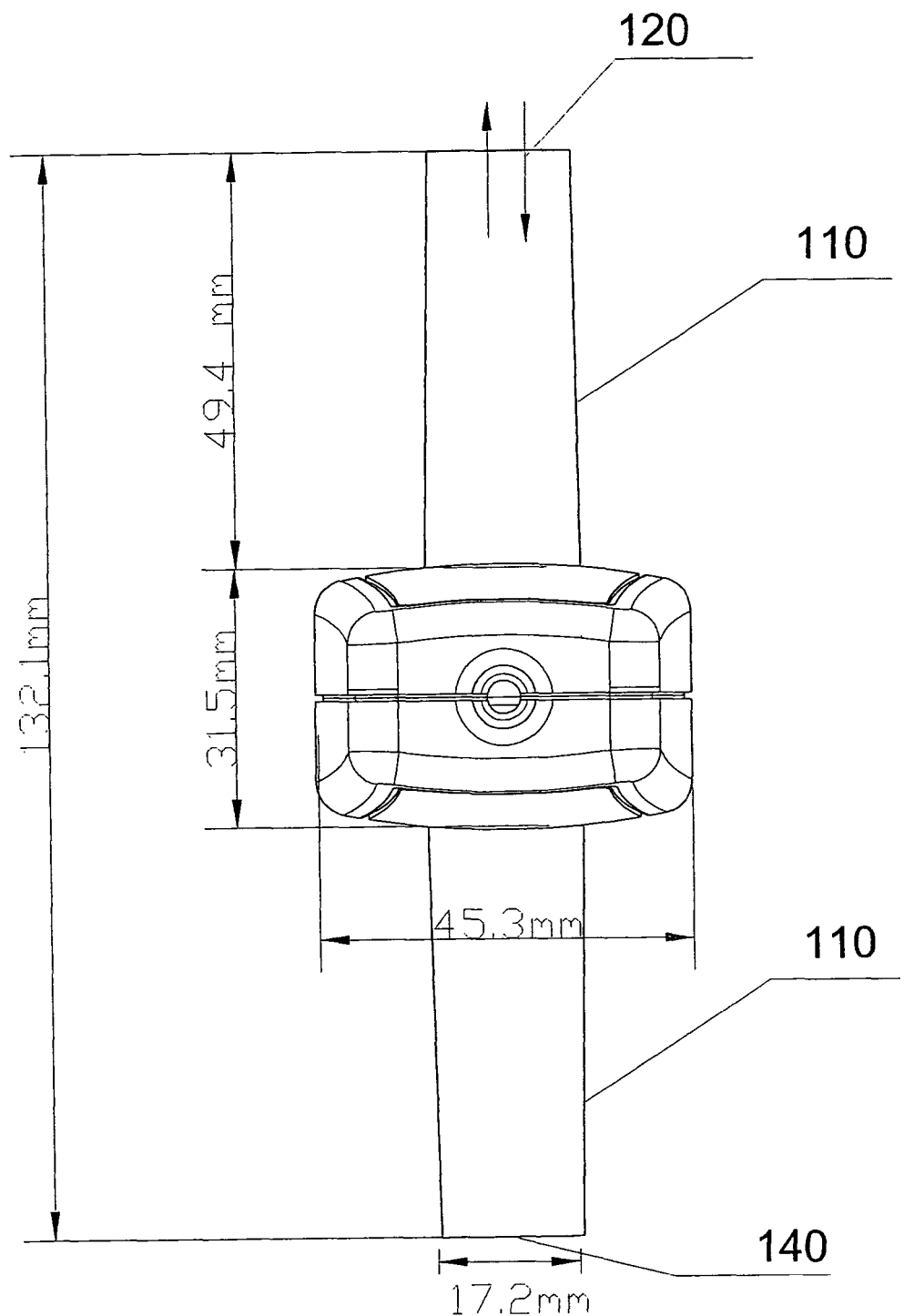

In FIGS. 2C-2E, location of inhalation into and exhalation from the apparatus is indicated by suitable arrows in proximity to a human face.

As shown, the tubes 150 may be circular in cross-section and the intersecting tubes 150 may be parallel, and perpendicular to the main tube 110. The second cross-section 210 may be a rectangular cross section having a first longer dimension and a second shorter dimension and the apertures 160 may be arranged along the first longer dimension. The intersecting tubes 150 may divide the cross-section of the main tube 110 into two.

Figure 5A:
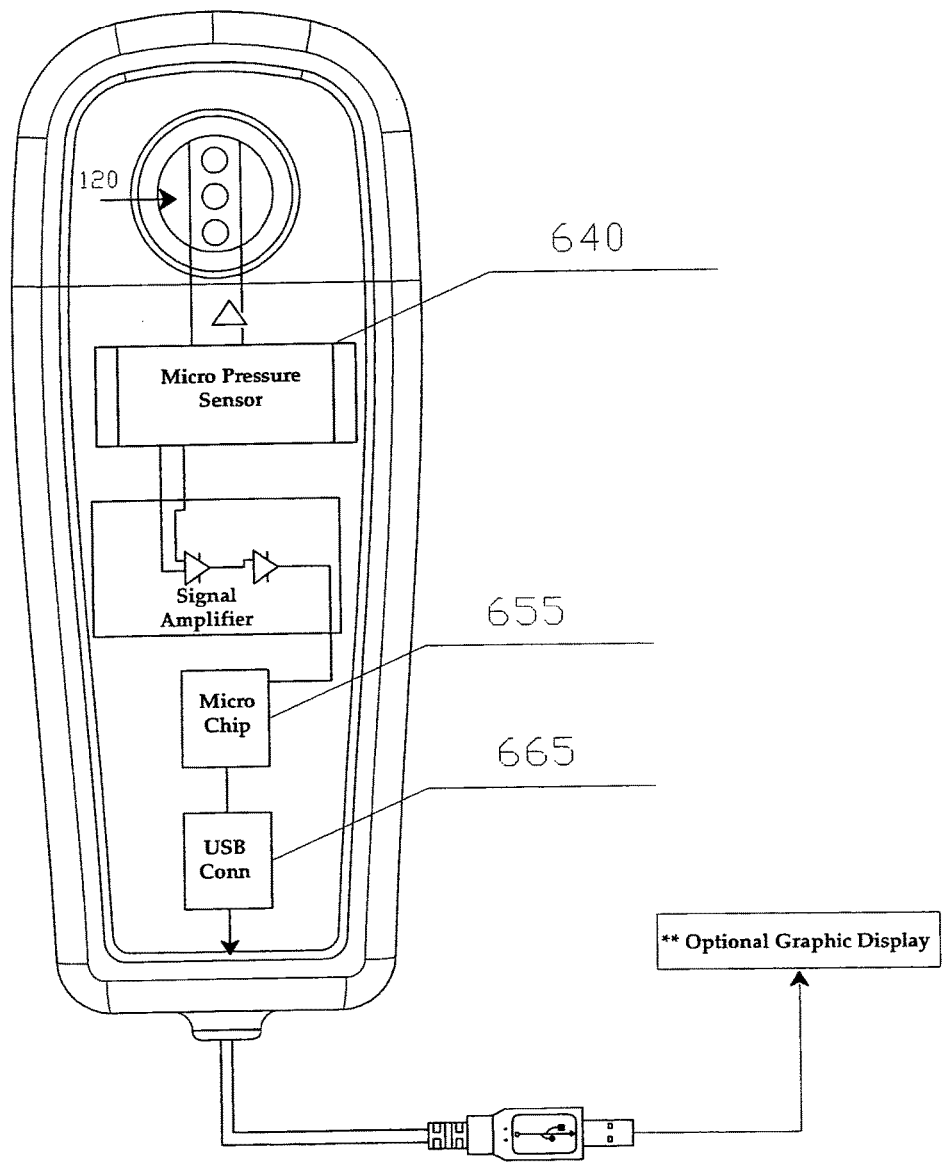
FIG. 5A is a spirometry system incorporating the spirometry apparatus shown and described above, all according to certain embodiments of the present invention.

FIG. 5A is a spirometry system incorporating the spirometry apparatus shown and described above, all according to certain embodiments of the present invention.

FIG. 5B illustrates a suitable interaction between the spirometry apparatus shown and described above and the pressure sensor of FIG. 5A.

FIGS. 5C-5E are cross-sectional front and reverse views of the spirometry apparatus of FIG. 5B.

Figure 6A:
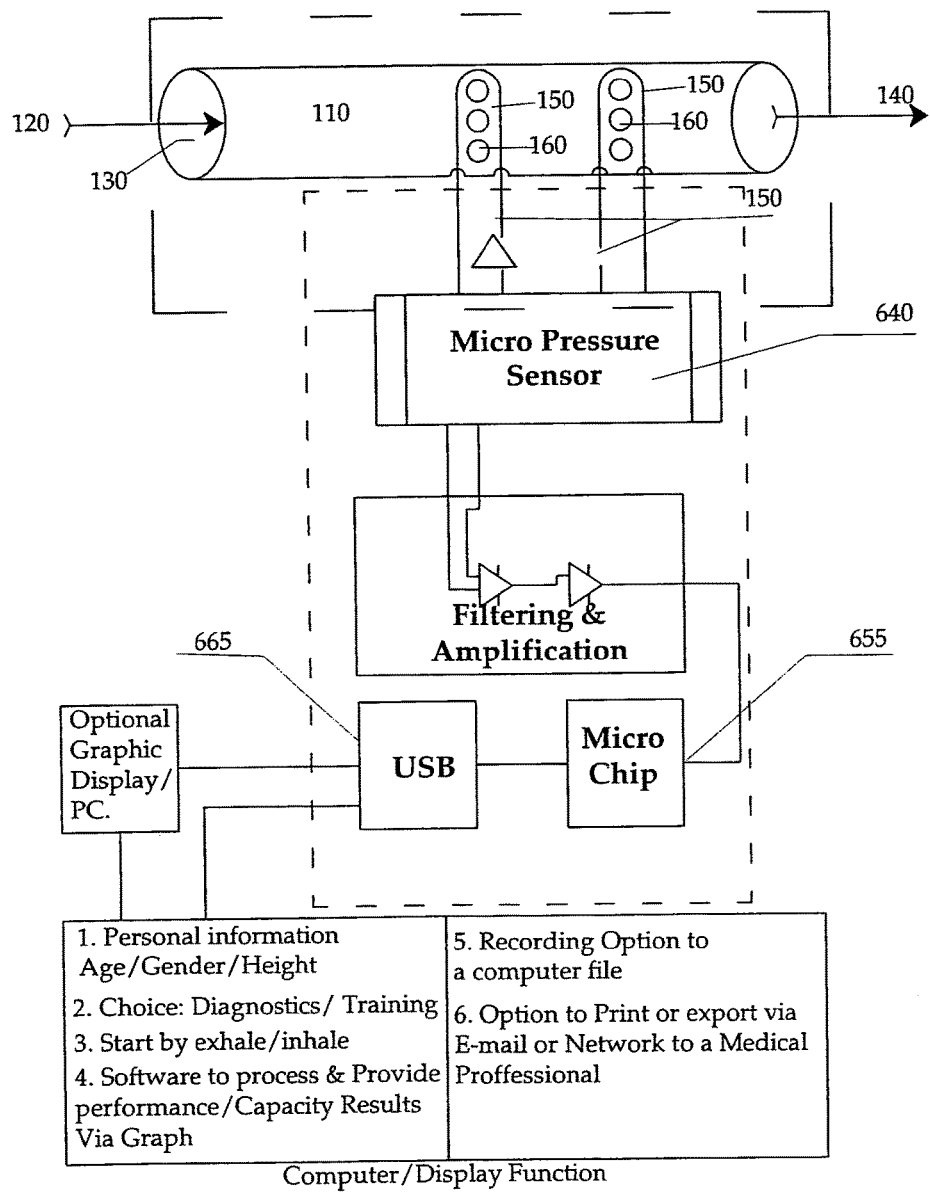
FIG. 6A-6B are systems for determining critical dimensions of and calibrating spirometer apparatus constructed and operative according to certain embodiments of the present invention.
Figure 6B:
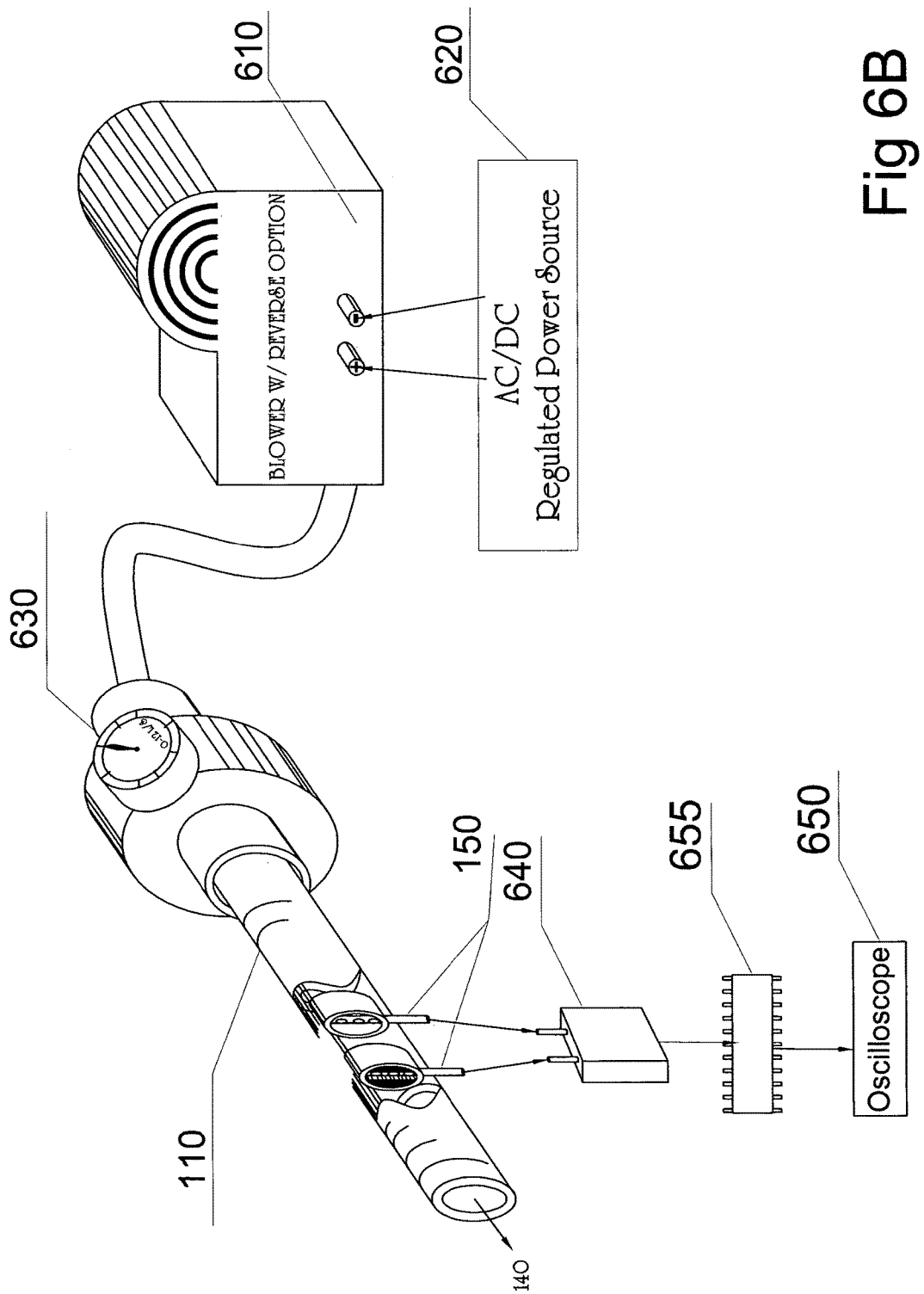

FIG. 6A-6B are systems for determining critical dimensions of and calibrating spirometer apparatus constructed and operative according to certain embodiments of the present invention.

FIG. 7 is an example of a digital output vs. air velocity table generated by the system of FIG. 6B.

Figure 8A:
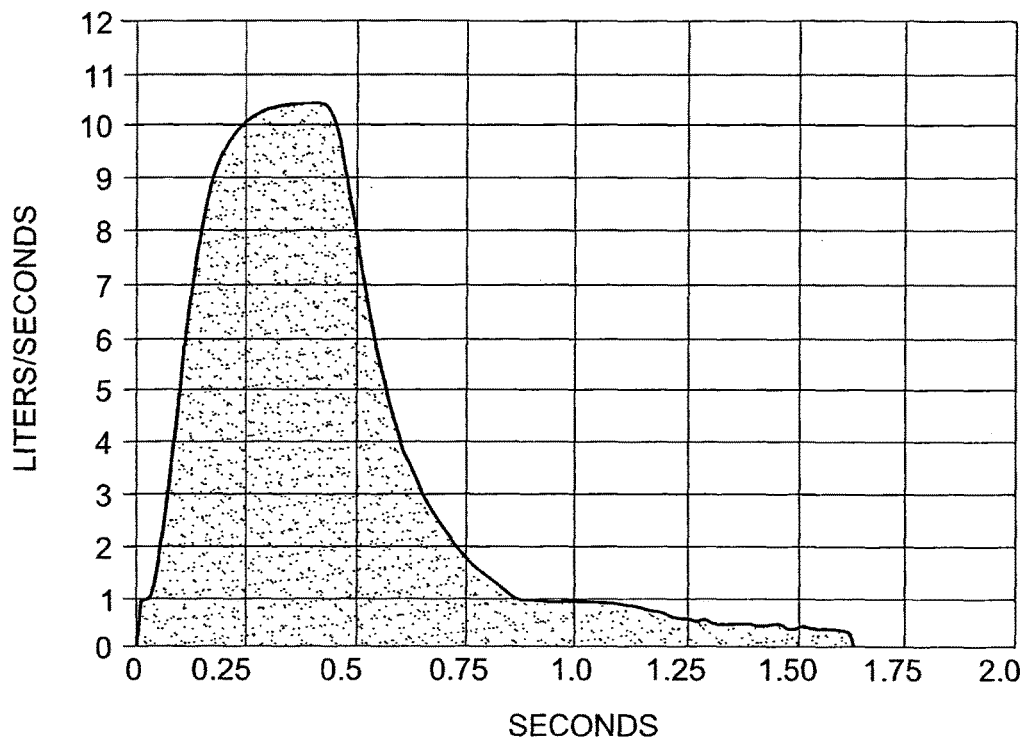
FIGS. 8A-8B are examples of air velocity vs. time graphs generated by spirometer apparatus constructed and operative according to certain embodiments of the present invention.
Figure 8B:
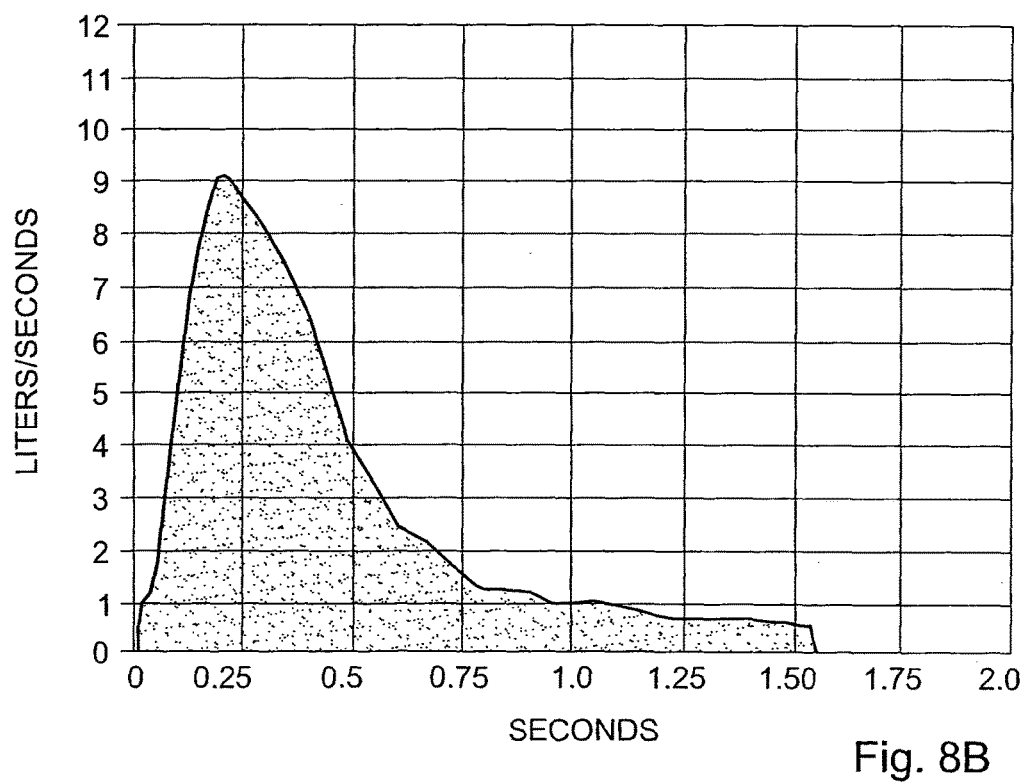

FIGS. 8A-8B are examples of air velocity vs. time graphs generated by spirometer apparatus constructed and operative according to certain embodiments of the present invention.

Typically, the dimensions of the main tunnel and its cross tubes are determined so as to prevent saturation within the desired operational range of, say, 0-12 liter/sec. Initial experiments for determining critical dimensions may be performed as shown in FIGS. 6A-8B. As shown, an inhaling and exhaling blower 610 operative in association with a suitable power source and DC voltage regulator such as an LE 3020 model commercially available from Lion Co. which have a site at: redlion.net/Products/DigitalandAnalog/Accessories/PowerSupplies may be used to supply controlled power to apparatus 620 constructed in accordance with certain embodiments of the present invention. The wind may be supplied at variable rates in the range of 0-12 liters per second which represents the range of human abilities. The wind speed may be gauged by an air velocity meter 630 such as a Meitav M4000 meter, Meitav having a site at meitavtec.com/product.aspx?PrdType=M4000MD&PrdCategory=HVAC%20Analyzerss.

The results of each sensed pressure drop may be measured, to confirm that there is no saturation, using a suitable differential pressure sensor 640 in conjunction with an oscilloscope 650 such as a Pintek DS203 having a website at globalmediapro.com/dp/A01LH6/Pintek-DS-203-Digital-Storage-Oscilloscope. If the results are indicative of saturation the openings in the cross pipes between location C1 (FIGS. 9A-10B) and the tube 150 closest to the inhale-exhale end 120 are gradually enlarged, until saturation is seen to have been eliminated. The cross-sectional dimension shown in FIG. 5C may for example be between 12 and 22 mm in the illustrated embodiment.

FIGS. 6A-6B illustrate a system used for calibrating the apparatus of the present invention once its critical dimensions have been determined e.g. as described above. As shown, the analog signal departing the differential pressure sensor 640 enters a micro-chip 655 which generates a 10 bit digital signal which enters a suitably programmed computer via a suitable connector such as a USB connector 665. A look-up table is constructed which stores the digital binary value provided by the micro-chip 655 responsive to each of a variety of wind inputs (in liter/sec) across a range of, say 0 to 12 liter/sec. An example of such a look-up table is illustrated in FIG. 7.

Typically, a polynomial is found, expressing output liter/sec values in terms of input 10 bit (e.g.) digital values since it is easier to determine output liter/sec values lying between digital values stored in the table by plugging into a typically 4-level polynomial rather than by interpolating repeatedly between entries in the table. A suitable software program is then generated to accumulate digital readings and, by plugging each of these into the polynomial, draw a liter/sec vs. time graph for each human subject, two examples of which are shown in FIGS. 8A-8B.

Using a spirometer similar to that shown herein, for example, the following polynomial was found to be suitable for computing air velocity in liter/sec:

$$-0.0018/100000000*H^4+0.04/1000000*H^3-0.294/10000*H^2+0.018*H+0.4,$$

where H are 10-bit digital values sampling a subject's performance. Typically, the subject's performance is read approximately 25 times per second, for approximately 2 seconds which is the approximate duration of inhalation or exhalation.

Respiration training software may be provided, for which the spirometer 100 provides feedback. The software may include some or all of the following functionalities: store and display personal information such as age, gender and height, allow a user to select a mode of operation such as diagnostics or respiration training, may then move into operational mode upon detection of exhaling or inhaling by a user, may process and generate a computer output representing performance and capacity results for the user, e.g. in graph form, may record outputs in a computer file for storage, and may optionally print results or export them via email or a suitable computer network to other medical professionals.

Figure 9A:
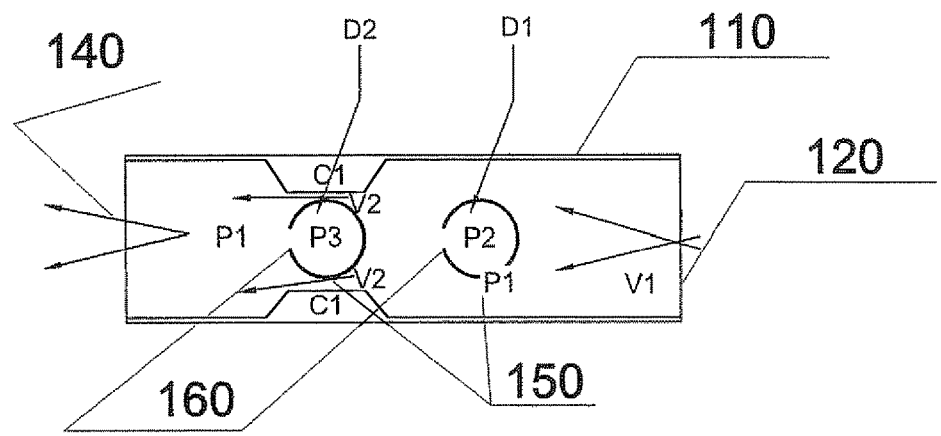
FIGS. 9A-9B are simplified top view and side sectional view diagrams, respectively, of spirometer apparatus constructed and operative in accordance with certain embodiments of the present invention into which a human subject is exhaling air.
Figure 9B:
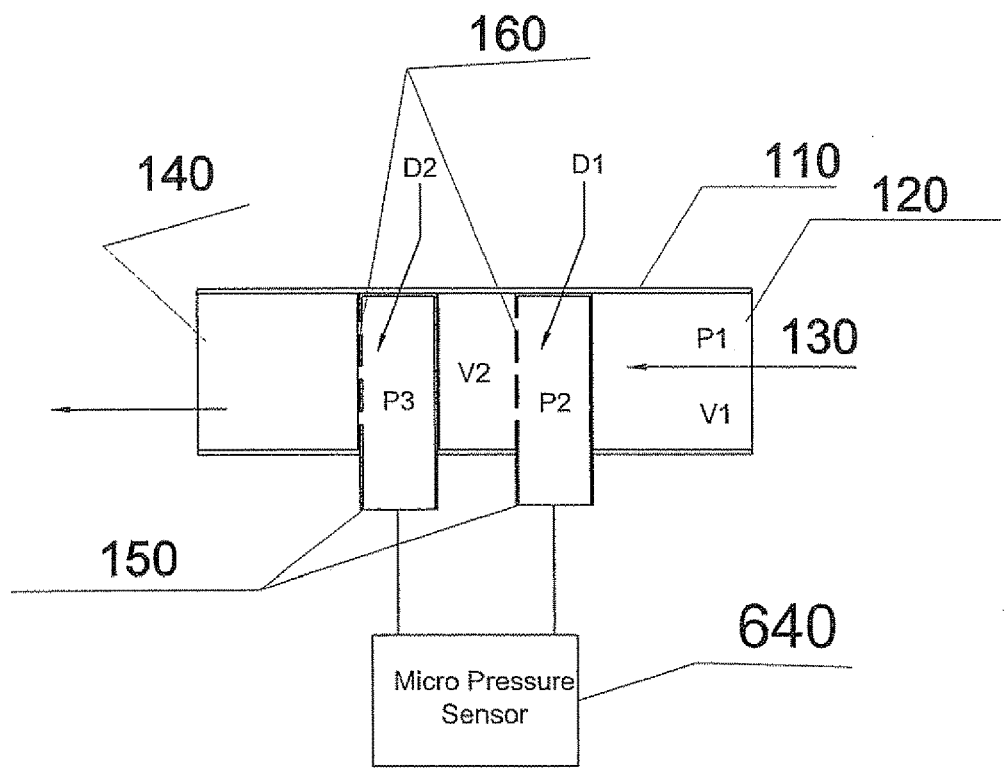

Reference is now made to FIGS. 9A-9B which are simplified top view and side sectional view diagrams, respectively, of spirometer apparatus constructed and operative in accordance with certain embodiments of the present invention into which a human subject is exhaling air as indicated by arrows. In the illustrated embodiments, two intersecting tubes 150 are shown, which are denoted D1 and D2 respectively.

The pressure at the partially blocked far end 140 of the main tube 110 is denoted P1 and the pressures within the tubes D1 and D2 are denoted P3 and P2 respectively; it is appreciated that P3 is smaller than P2. Air velocities are denoted by V; it is appreciated that V2 is far greater than V1.

Figure 10A:
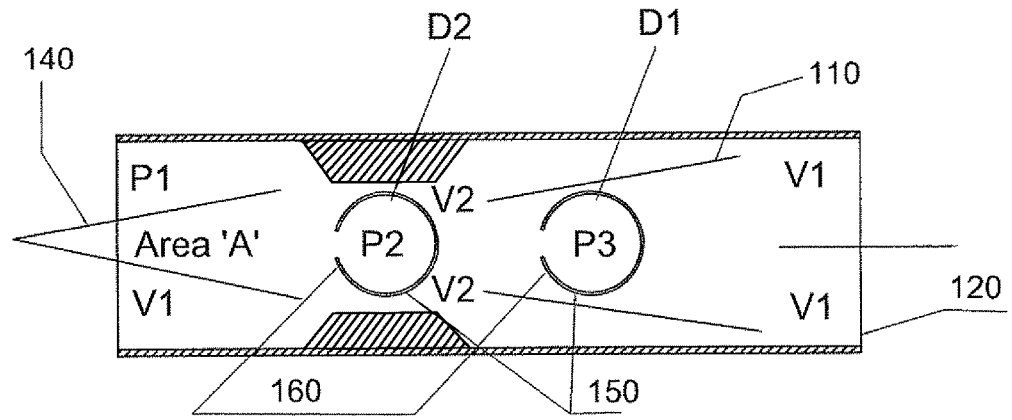
FIGS. 10A-10B are simplified top view and side sectional view diagrams, respectively, of spirometer apparatus constructed and operative in accordance with certain embodiments of the present invention from which a human subject is inhaling air.
Figure 10B:
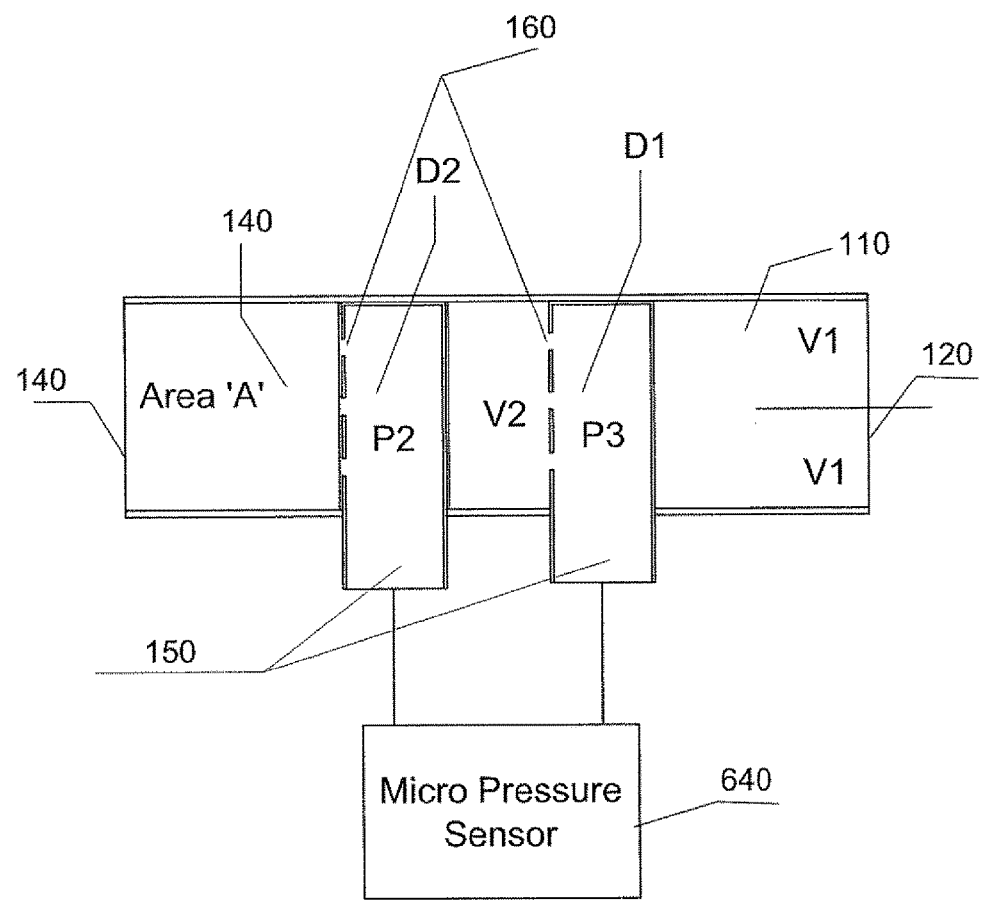

Reference is now made to FIGS. 10A-10B which are simplified top view and side sectional view diagrams, respectively, of spirometer apparatus constructed and operative in accordance with certain embodiments of the present invention from which a human subject is inhaling air as indicated by arrows.

Reference is now made to FIGS. 9A-9B which are simplified top view and side sectional view diagrams, respectively, of spirometer apparatus constructed and operative in accordance with certain embodiments of the present invention into which a human subject is exhaling air as indicated by arrows. In the illustrated embodiments, two intersecting tubes 150 are shown, which are denoted D1 and D2 respectively. The pressure at the partially blocked far end 140 of the main tube 110 is denoted P1 and the pressures within the tubes D1 and D2 are denoted P3 and P2 respectively; it is appreciated that P3 is smaller than P2. Air velocities are denoted by V; it is appreciated that V2 is far greater than V1.

Reference is now made to FIGS. 10A-10B which are simplified top view and side sectional view diagrams, respectively, of spirometer apparatus constructed and operative in accordance with certain embodiments of the present invention from which a human subject is inhaling air as indicated by arrows. It is appreciated that whereas P2 is greater than P3 when a subject exhales as in FIGS. 9A-9B, when a subject inhales as in FIGS. 10A-10B, P3 is greater than P2.

It is appreciated that software components of the present invention including programs and data may, if desired, be implemented in ROM (read only memory) form including CD-ROMs, EPROMs and EEPROMs, or may be stored in any other suitable computer-readable medium such as but not limited to disks of various kinds, cards of various kinds and RAMs. Components described herein as software may, alternatively, be implemented wholly or partly in hardware, if desired, using conventional techniques. Conversely, components described herein as hardware may, alternatively, be implemented wholly or partly in software, if desired, using conventional techniques.

Included in the scope of the present invention, inter alia, are electromagnetic signals carrying computer-readable instructions for performing any or all of the steps of any of the methods shown and described herein, in any suitable order; machine-readable instructions for performing any or all of the steps of any of the methods shown and described herein, in any suitable order; program storage devices readable by machine, tangibly embodying a program of instructions executable by the machine to perform any or all of the steps of any of the methods shown and described herein, in any suitable order; a computer program product comprising a computer useable medium having computer readable program code having embodied therein, and/or including computer readable program code for performing, any or all of the steps of any of the methods shown and described herein, in any suitable order; any technical effects brought about by any or all of the steps of any of the methods shown and described herein, when performed in any suitable order; any suitable apparatus or device or combination of such, programmed to perform, alone or in combination, any or all of the steps of any of the methods shown and described herein, in any suitable order; information storage devices or physical records, such as disks or hard drives, causing a computer or other device to be configured so as to carry out any or all of the steps of any of the methods shown and described herein, in any suitable order; a program pre-stored e.g. in memory or on an information network such as the Internet, before or after being downloaded, which embodies any or all of the steps of any of the methods shown and described herein, in any suitable order, and the method of uploading or downloading such, and a system including server/s and/or client/s for using such; and hardware which performs any or all of the steps of any of the methods shown and described herein, in any suitable order, either alone or in conjunction with software.

Features of the present invention which are described in the context of separate embodiments may also be provided in combination in a single embodiment. Conversely, features of the invention, including method steps, which are described for brevity in the context of a single embodiment or in a certain order may be provided separately or in any suitable subcombination or in a different order. "e.g." is used herein in the sense of a specific example which is not intended to be limiting. Devices, apparatus or systems shown coupled in any of the drawings may in fact be integrated into a single platform in certain embodiments or may be coupled via any appropriate wired or wireless coupling such as but not limited to optical fiber, Ethernet, Wireless LAN, HomePNA, power line communication, cell phone, PDA, Blackberry GPRS, Satellite including GPS, or other mobile delivery.

The invention claimed is:

1. A spirometer apparatus comprising:
    a Venturi tube having a wall and an interior, provided at a first end with a mouthpiece suitable to allow a user to exhale and inhale therethrough, and a second end suitable to allow-the inlet and outlet of air;
    a constricted section of the Venturi tube located at a first distance from the mouthpiece end of the Venturi tube and having a first internal cross section, and at a second distance from the second end of the Venturi tube, wherein the first distance is greater than the second distance;
    two elongated vessels located internally completely within the interior of the Venturi tube and positioned vertically when the Venturi tube is essentially horizontal in a use orientation, each of said two vessels having a plurality of evenly spaced openings that are all positioned within the interior of the Venturi tube and intersecting the wall of the Venturi tube at two diametrically opposite regions to accommodate positioning of said plurality of openings within the interior of the Venturi tube and adapted for the air from an inlet to transit the two elongated vessels in series, a first vessel of said two elongated vessels having a first external cross-section that is smaller than the first internal cross-section, the second of said two elongated vessels having a second external cross-section, the second external cross-section being smaller than the first external cross-section, thereby to cause a pressure drop between the first and second distances during Inhale and during exhale;
    a pressure sensing apparatus connected to said two elongated vessels, suitable to measure the pressure drop;
    wherein a first of said two elongated vessels intersects the wall of the Venturi tube at the constricted section thereof; and
    wherein a second of said two elongated vessels intersects the wall of the Venturi tube at a location closer to the mouthpiece end than the first elongated vessel; and
    wherein the two elongated vessels located internally within the main interior and intersect the internal surface of the Venturi tube so as to divide the cross-section of the Venturi tube in two.

2. The apparatus according to claim 1, wherein the first internal vessel openings are located opposite the direction of air exhaled from the mouthpiece.

3. The apparatus according to claim 1, wherein each of said elongated vessels is a tube.

4. The apparatus according to claim 3, wherein at least one of the tubes is circular in cross-section.

5. The apparatus according to claim 1, wherein the axes of said internal vessels are parallel.

6. The apparatus according to claim 1, wherein the axes of the elongated vessels are perpendicular to the axis of the Venturi tube.

7. The apparatus according to claim 1, wherein said plurality of openings includes 3 or 4 openings.

8. The apparatus according to claim 1 wherein said plurality of openings on the elongated vessels are uniformly spaced so as to cause each opening on one elongate vessel to be horizontally aligned with a corresponding opening on the other elongated vessel.

9. The apparatus according to claim 1, further comprising respiration training software for which the pressure sensing apparatus provides feedback.

10. The apparatus according to claim 1, wherein each of said elongated vessels includes a first open end communicating with said pressure sensing apparatus and a second sealed end.

11. The apparatus according to claim 1, wherein the cross section of the elongated vessels is selected from circular, oval, and polygonal.

12. The apparatus according to claim 1, wherein the Venturi tube has a diameter and the first and second elongated vessels are located at first and second distances away from the first and second ends of the Venturi tube, respectively, said first and second distances equaling at least three times the diameter of the Venturi tube to ensure that air flow through the Venturi tube will be generally parallel to its axis and to thereby enhance uniformity of pressure differential measurements.

13. The apparatus according to claim 1, wherein the openings of the first and second elongated vessels face the second end of the Venturi tube.

14. The apparatus according to claim 1, wherein the Venturi tube and the first and second elongated vessels are dimensioned so as to prevent measurement saturation for a desired operational range.

15. The apparatus according to claim 9, wherein a signal generated by the pressure sensing apparatus is an analog signal, the apparatus further comprising a micro-chip for receiving said analog signal and generating therefrom a digital signal; and a processor programmed with the respiration training software for processing said digital signal to generate performance and capacity results for a user, with feedback.

16. The apparatus according to claim 15, wherein the processor is also operative to process said digital signal to generate an output and to compare said output with a value of a look-up table that is responsive to an air input into the Venturi tube that resulted in the measured air pressure differential, for use in calibrating the apparatus.

17. The apparatus according to claim 15, further comprising digital communication components for exporting the digitally processed results to other medical professionals to perform diagnostic analysis.

* * * * *